(12) United States Patent
Bulthuis et al.

(10) Patent No.: US 6,432,686 B1
(45) Date of Patent: Aug. 13, 2002

(54) METHOD FOR THE PRODUCTION OF 1,3-PROPANEDIOL BY RECOMBINANT ORGANISMS COMPRISING GENES FOR VITAMIN B12 TRANSPORT

(75) Inventors: Ben A. Bulthuis, Hoofddorp (NL); Gregory M. Whited, Belmont; Donald E. Trimbur, Redwood City, both of CA (US); Anthony A. Gatenby, Wilmington, DE (US)

(73) Assignees: E. I. du Pont de Nemours and Company, Wilmington, DE (US); Genencor International, Palo Alto, CA (US)

( * ) Notice: Subject to any disclaimer, the term of this patent is extended or adjusted under 35 U.S.C. 154(b) by 0 days.

(21) Appl. No.: 09/307,973

(22) Filed: May 10, 1999

Related U.S. Application Data

(60) Provisional application No. 60/085,190, filed on May 12, 1998.

(51) Int. Cl.$^7$ ............... C12P 7/18; C12N 1/20; C12N 15/00
(52) U.S. Cl. ........ 435/158; 435/252.3; 435/320.1
(58) Field of Search ............. 435/158, 252.3, 435/320.1; 536/23.2

(56) References Cited

U.S. PATENT DOCUMENTS

| | | | |
|---|---|---|---|
| 5,599,689 A | 2/1997 | Haynie et al. | 435/42 |
| 5,633,362 A | 5/1997 | Nagarajan et al. | 536/23.1 |
| 5,686,276 A | * 11/1997 | Laffend et al. | 435/158 |
| 5,686,279 A | 11/1997 | Finer et al. | 435/172.3 |

FOREIGN PATENT DOCUMENTS

| | | |
|---|---|---|
| WO | WO 87/01391 | 3/1987 |
| WO | WO 96 35795 A | 11/1996 |
| WO | WO98/21339 | 5/1998 |
| WO | WO 98/21340 | 5/1998 |
| WO | WO 98/21341 | 5/1998 |

OTHER PUBLICATIONS

Rioux et al., J. bacteriol., 171/6, 2986–2993, Jun. 1989.*
Heller et al., J. Bacteriol., 161, 904–908, Mar. 1985.*
Freidrich et al., J. Bacteriol., 167, 928–908, Sep. 1986.*
Wei et al., Res. Microbiol., 143, 459–466, Apr. 1992.*

Cameron et al., Cloning and Analysis of Genes Involved in Coenzyme $B_{12}$ Biosynthesis in *Pseudomonas denitrificans*, Journal of Bacteriology, Jan. 1989 p 547–557.

Blanche et al., Purification and Characterization of S–Adenosyl–L–Methionine: Uroporphyrinogen III Methyltransferase from *Pseudomonas dennitrificans* Journal of Bacteriology Aug. 1989, 4222–4231.

Brey et al., Cloning of Multiple Genes Involved with Cobalamin (Vitamin $B_{12}$) Biosynthesis in *Bacillus megaterium*, Journal of Bacteriology, Aug., 1986, vol. 167. No. 2.

Jeter et al., Cobalamin (Vitamin B12) Biosynthetic Genes of *Salmonella typhimurium*, Journal of Bacteriology., Jul. 1987, vol. 169, No. 7.

Crouzet et al., Nucleotide Sequence of a *Pseudomonas denitrificans* 5,4–Kilobase DNA Fragment Containing Five cob Genes and Identification of Structural Genes Encoding S–Adenosyl–L–Methionine: Journal of Bacteriology 1990, vol. 172, No. 10 p5968–5979.

Crouzet et al., Genetic and Sequence Analysis of an 8.7 Kilobase *Pseudomonas denitrificans* Fragment Carrying Eight Genes Involved in Transformation of Precorrin–2 to Cobyrinic Acid, Journal of Bacteriology, Oct. 1990, vol. 172, No. 19, p. 5980–5990.

DeVeaux et al., Transport of Vitamin $B_{12}$ in *Escherichia coli*: Cloning of the btu CD Region, *Journal of Bacteriology*, vol. 162, No. 3, 888–897, Jun. 1985.

* cited by examiner

*Primary Examiner*—Rebecca E. Prouty
*Assistant Examiner*—Maryam Monshipouri

(57) ABSTRACT

Recombinant organisms are provided comprising genes encoding genes encoding glycerol dehydratase, 1,3-propanediol oxidoreductase, a gene encoding vitamin $B_{12}$ receptor precursor(BtuB), a gene encoding vitamin $B_{12}$ transport system permease protein(BtuC) and a gene encoding vitamin $B_{12}$ transport ATP-binding protein (BtuD). The recombinant microorganism is contacted with a carbon substrate and 1,3-propanediol is isolated from the growth media.

13 Claims, No Drawings

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 1845 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
ATGATTAAAA AAGCTTCCCT GCTGACGGCG TGTTCCGTCA CGGCATTTTC CGCTTGGGCA        60

CAGGATACCA GCCCGGATAC TCTCGTCGTT ACTGCTAACC GTTTTGAACA GCCGCGCAGC       120

ACTGTGCTTG CACCAACCAC CGTTGTGACC CGTCAGGATA TCGACCGCTG GCAGTCGACC       180

TCGGTCAATG ATGTGCTGCG CCGTCTTCCG GGCGTCGATA TCACCCAAAA CGGCGGTTCA       240

GGTCAGCTCT CATCTATTTT TATTCGCGGT ACAAATGCCA GTCATGTGTT GGTGTTAATT       300

GATGGCGTAC GCCTGAATCT GGCGGGGGTG AGTGGTTCTG CCGACCTTAG CCAGTTCCCT       360

ATTGCGCTTG TCCAGCGTGT TGAATATATC CGTGGGCCGC GCTCCGCTGT TTATGGTTCC       420

GATGCAATAG GCGGGGTGGT GAATATCATC ACGACGCGCG ATGAACCCGG AACGGAAATT       480

TCAGGAGGGT GGGGAAGCAA TAGTTATCAG AACTATGATG TCTCTACGCA GCAACAACTG       540
```

| | | | | |
|---|---|---|---|---|
|GGGGATAAGA|CACGGGTAAC|GCTGTTGGGC|GATTATGCCC|ATACTCATGG TTATGATGTT| 600
|GTTGCCTATG|GTAATACCGG|AACGCAAGCG|CAGACAGATA|ACGATGGTTT TTTAAGTAAA| 660
|ACGCTTTATG|GCGCGCTGGA|GCATAACTTT|ACTGATGCCT|GGAGCGGCTT TGTGCGCGGC| 720
|TATGGCTATG|ATAACCGTAC|CAATTATGAC|GCGTATTATT|CTCCCGGTTC ACCGTTGCTC| 780
|GATACCCGTA|AACTCTATAG|CCAAAGTTGG|GACGCCGGGC|TGCGCTATAA CGGCGAACTG| 840
|ATTAAATCAC|AACTCATTAC|CAGCTATAGC|CATAGCAAAG|ATTACAACTA CGATCCCCAT| 900
|TATGGTCGTT|ATGATTCGTC|GGCGACGCTC|GATGAGATGA|AGCAATACAC CGTCCAGTGG| 960
|GCAAACAATG|TCATCGTTGG|TCACGGTAGT|ATTGGTGCGG|GTGTCGACTG GCAGAAACAG|1020
|ACTACGACGC|CGGGTACAGG|TTATGTTGAG|GATGGATATG|ATCAACGTAA TACCGGCATC|1080
|TATCTGACCG|GGCTGCAACA|AGTCGGCGAT|TTTACCTTTG|AAGGCGCCAG ACGCAGTGAC|1140
|GATAACTCAC|AGTTTGGTCG|TCATGGAACC|TGGCAAACCA|GCGCCGGTTG GGAATTCATC|1200
|GAAGGTTATC|GCTTCATTGC|TTCCTACGGG|ACATCTTATA|AGGCACCAAA TCTGGGGCAA|1260
|CTGTATGGCT|TCTACGGAAA|TCCGAATCTG|GACCCGGAGA|AAAGCAAACA GTGGGAAGGC|1320
|GCGTTTGAAG|GCTTAACCGC|TGGGGTGAAC|TGGCGTATTT|CCGGATATCG TAACGATGTC|1380
|AGTGACTTGA|TCGATTATGA|TGATCACACC|CTGAAATATT|ACAACGAAGG GAAAGCGCGG|1440
|ATTAAGGGCG|TCGAGGCGAC|CGCCAATTTT|GATACCGGAC|CACTGACGCA TACTGTGAGT|1500
|TATGATTATG|TCGATGCGCG|CAATGCGATT|ACCGACACGC|CGTTGTTACG CCGTGCTAAA|1560
|CAGCAGGTGA|ATACCAGCT|CGACTGGCAG|TTGTATGACT|TCGACTGGGG TATTACTTAT|1620
|CAGTATTTAG|GCACTCGCTA|TGATAAGGAT|TACTCATCTT|ATCCTTATCA AACCGTTAAA|1680
|ATGGGCGGTG|TGAGCTTGTG|GGATCTTGCG|GTTGCGTATC|CGGTCACCTC TCACCTGACA|1740
|GTTCGTGGTA|AAATAGCCAA|CCTGTTCGAC|AAAGATTATG|AGACAGTCTA TGGCTACCAA|1800
|ACTGCAGGAC|GGGAATACAC|CTTGTCTGGC|AGCTACACCT|TCTGA|1845

(2) INFORMATION FOR SEQ ID NO:2:

(i) SEQUENCE CHARACTERISTICS:
        (A) LENGTH: 1844 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

| | | | | |
|---|---|---|---|---|
|ATGATTAAAA|AAGCTACGCT|GCTGACGGCG|TTCTCCGTCA|CGGCCTTTTC CGCTTGGGCG| 60
|CAGGACACTA|GCCCGGATAC|CCTGGTTGTC|ACCGCCAACC|GTTTTCAGCA GCCGCGCAGC|120
|GCGGTTCTGG|CGCCCGTTAC|CATCGTGACG|CGTCAGGATA|TTGAACGCTG GCAATCGACC|180
|TCCGTAAATG|ATGTTCTGCG|CCGTTTGCCT|GGCGTCGATA|TTGCGCAGAG CGGCGGCGCG|240
|CGACAAAACT|CCTCCATTTT|CATTCGCGGC|ACCAACTCCA|GCCATGTACT GGTATTGATT|300
|GACGGCGTGC|GTCTGAATTT|AGCAGGCGTG|AGCGGGTCCG|CCGATCTCAG CCAGTTCCCG|360
|GTGTCGCTGG|TACAGCGTAT|TGAATATATA|CGCGGTCCGC|CCTCCGCTAT TTATGGTTCC|420
|GATGCTATCG|GCGGCGTAGT|GAATATCATT|ACGACGCGCG|ATAACCCAGG CACAGAATTA|480
|ACCGCTGGAT|GGGGAAGCAA|TAGCTACCAG|AATTACGACA|TCTCGACGCA ACAGCAACTT|540

-continued

```
GGCGAAATCA CGCGGGCGAC GTTGATCGGC GATTACGAAT ACACCAAAGG GTTTGACGTG    600

GTAGCGAAAG GCGGTACCGG GATGCAGGCG CAGCCTGACC GGGACGGCTT TTTGAGTAAA    660

ACGCTTTATG GCGCGTTAGA GCATACCTTT TCTGATCGCT GGAGCGGATT CGTGCGTGGT    720

TATGGCTACG ATAACCGTAC CGATTACGAC GCCTATTACT CGCCGGGCTC GCCGCTGATT    780

GATACACGCA AACTTTATAG CCAAAGCTGG GACGCCGGGC TGCACTTTAA TGGCGAAAGT    840

ATTCAGTCTC AGCTGGTTTC AAGCTATAGC CACAGTAAAG ATTACAACTA TGATCCGCAC    900

TATGGCCGGT ATGATACCTC CGCCACGCTG GATGAGATGA AACAGTACAA TGTTCAATGG    960

ACCAACAGTG TGGTCGTGGG GACGGTAATG TTGGGGCGGG CGTAGACTGG CAGAAACAGA   1020

CTACCACGCC AGGTACCGGC TATGTGCCCG AGGGATATGA CCAGCGTAAT ACCGGGGTTT   1080

ACCTGACAGG ATTACAACAG TTGGGTGACT TCACTCTGGA AGCGGCGGCG CGCAGTGATG   1140

ACAACTCCCA GTTTGGTCGT CATGGTACAT GGCAAACCAG CGCGGGATGG GAGTTTATAG   1200

AAGGTTATCG CTTTATTGCC TCCTACGGAA CCTCCTACAA AGCGCCTAAT TTGGGCCAAC   1260

TGTATGGTTA TTACGGTAAT CCGAACCTGA ATCCTGAAAA GAGTAAACAG TGGGAAGGCG   1320

CATTTGAAGG GCTAACCGCT GGCGTCAGCT GGCGTATTTC AGGTTATCGT AACGATATTA   1380

ATGACATGAT CGATTATGAC GATCATCTGC AAAAATATTA CAACGAAGGT AAGGCGCGCA   1440

TTAAAGGTAT TGAGGCGACG GCGAATTTCG ATACCGGACC GTTAACGCAT ACGGTCAGTT   1500

ATGATTACGT TGATGCGCGT AATGCGATTA CCGATACGCC ATTACCCCGG CGTTCCAAAC   1560

AGATGGCAAA ATATCAACTT GACTGGGACG TTTACGATTT TGACTGGGGG ATGACATATC   1620

AATACCTTGG TTCCCGCTAT GATTCGGATT ACTCCGCTTA CCCATACCGG ACAGTAAAAA   1680

TGGGCGGCGT CAGTTTATGG GATCTTACGG TTGCATATCC GGTCACCTCA CATCTGACAG   1740

TTCGTGGTAA AATAGCCAAC CTGTTCGACA AGATTACGA GACAGTTTAT GGCTACCAAA    1800

CTGCAGGACG AGAATACACC TTGTCTGGCA GCTACACCTT CTGA                     1844
```

(2) INFORMATION FOR SEQ ID NO:3:

(i) SEQUENCE CHARACTERISTICS:
        (A) LENGTH: 981 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
ATGCTGACAC TTGCCCGCCA ACAACAGCGA CAAAATATTC GCTGGTTATT ATGCCTGTCA     60

GTTTTGATGC TGCTGGCGCT TCTCTTAAGC CTTTGCGCCG TGAACAATG GATCTCGCCA    120

GGTGACTGGT TTACTCCTCG TGGCGAACTG TTCGTCTGGC AAATTCGCCT GCCACGTACG    180

CTGGCTGTAT TGCTGGTTGG TGCGGCGCTG GCTATATCCG GCGCTGTAAT GCAGGCGTTG    240

TTTGAAAATC CTCTGGCAGA ACCTGGACTA CTTGGCGTCT CTAACGGCGC AGGCGTGGGG    300

CTTATCGCCG CGGTATTGCT TGGGCAAGGG CTAACTCCCA ACTGGGCGCT AGGGCTGTGT    360

GCGATTCGTG GCGCGCTTAT CATCACTTTA ATACTCTTAC GTTTCGCCCG TCGTCATCTT    420

TCGACCAGTC GGTTATTGCT GGCTGGCGTT GCATTAGGGA TTATCTGTAG CGCACTAATG    480

ACGTGGGCTA TCTACTTTTC CACCTCAGTT GATTTGCGTC AGCTGATGTA CTGGATGATG    540
```

```
GGCGGTTTTG GCGGCGTAGA CTGGCGGCAA AGCTGGCTGA TGCTGGCATT GATCCCCGTG    600

TTGTTGTGGA TCTGTTGTCA GTCCAGGCCG ATGAATATGT TAGCACTTGG CGAGATCTCG    660

GCGCGGCAAC TGGGTTTACC CCTGTGGTTC TGGCGCAATG TGCTGGTGGC AGCGACCGGC    720

TGGATGGTTG GCGTCAGTGT GGCGCTGGCG GGTGCTATCG GCTTTATTGG TCTGGTGATC    780

CCCCATATTC TCCGGTTGTG TGGTTTAACC GATCATCGCG TATTACTTCC CGGCTGCGCG    840

CTGGCAGGGG CGAGCGCATT GCTGCTGGCC GATATTGTAG CGCGCCTGGC ATTAGCTGCC    900

GCAGAGCTGC CTATTGGCGT GGTCACCGCA ACGTTAGGTG CGCCGGTGTT TATCTGGTTA    960

TTGTTAAAAG CAGGACGTTA G                                              981
```

(2) INFORMATION FOR SEQ ID NO:4:

(i) SEQUENCE CHARACTERISTICS:
        (A) LENGTH: 750 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
ATGTCTATTG TGATGCAGTT ACAAGATGTT GCGGAATCTA CCCGCCTGGG GCCGCTTTCT     60

GGCGAGGTTC GGGCTGGGGA GATCCTGCAC CTGGTGGGGC CGAATGGCGC GGGTAAGAGT    120

ACCTTACTGG CGCGAATGGC CGGAATGACC AGCGGTAAGG GAAGCATTCA GTTCGCGGGG    180

CAACCACTGG AAGCATGGTC CGCAACAAAA CTCGCGCTGC ATCGCGCCTA TCTTTCACAA    240

CAGCAGACGC CGCCGTTTGC AACGCCGGTC TGGCACTACC TGACACTGCA TCAGCACGAT    300

AAAACGCGTA CCGAACTACT GAATGATGTC GCAGGGGCGC TGGCTCTTGA TGACAAACTC    360

GGACGTAGCA CCAATCAACT TTCCGGCGGT GAATGGCAAC GCGTACGTCT TGCTGCGGTG    420

GTGTTGCAAA TCACACCACA AGCCAATCCC GCAGGCCAAT TGCTGCTTCT TGATGAGCCG    480

ATGAACAGTC TTGATGTTGC GCAACAAAGT GCGTTAGACA AAATTCTGAG CGCGCTGTGT    540

CAGCAAGGAC TGGCGATTGT GATGAGCAGT CACGATCTCA ACCACACATT GCGTCATGCG    600

CATCGGGCGT GGTTGCTAAA AGGTGGAAAA ATGCTGGCCA GTGGACGCAG GAAGAGGTG    660

CTCACGCCGC CAAATCTGGC GCAGGCCTAT GGGATGAATT TCGCCGTCT GGATATCGAA    720

GGTCACAGAA TGCTGATTTC GACCATCTGA                                    750
```

(2) INFORMATION FOR SEQ ID NO:5:

(i) SEQUENCE CHARACTERISTICS:
        (A) LENGTH: 552 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
ATGCAAGATT CCATTCTGAC GACCGTAGTG AAAGATATCG ACGGTGAAGT GACCACGCTG     60

GAGAAGTTCG CCGGTAATGT GCTGTTGATT GTCAATGTCG CCTCAAAGTG TGGCTTAACG    120
```

```
CCGCAATATG AGCAGTTGGA GAATATTCAG AAAGCCTGGG TCGATCGAGG TTTTATGGTG      180

CTGGGATTCC CGTGCAACCA GTTTCTGGAA CAAGAACCGG GCAGCGATGA AGAGATTAAA      240

ACTTACTGTA CCACCACATG GGGGGTGACG TTCCCGATGT TCAGTAAGAT TGAAGTTAAT      300

GGCGAAGGAC GCCATCCGCT GTATCAAAAA TTGATTGCCG CAGCGCCGAC CGCAGTCGCG      360

CCGGAAGAGA GCGGATTCTA TGCCCGTATG GTCAGCAAAG GCCGTGCACC GCTGTACCCG      420

GATGATATTT TATGGAATTT TGAAAAATTC CTGGTTGGCA GGGACGGAAA AGTCATCCAG      480

CGTTTTTCCC CGGATATGAC GCCGGAAGAT CCCATTGTGA TGGAAAGCAT TAAACTGGCG      540

TTGGCAAAAT AA                                                          552
```

(2) INFORMATION FOR SEQ ID NO:6:

(i) SEQUENCE CHARACTERISTICS:
        (A) LENGTH: 1668 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
ATGAAAAGAT CAAAACGATT TGCAGTACTG GCCCAGCGCC CCGTCAATCA GGACGGGCTG       60

ATTGGCGAGT GGCCTGAAGA GGGGCTGATC GCCATGGACA GCCCCTTTGA CCCGGTCTCT      120

TCAGTAAAAG TGGACAACGG TCTGATCGTC GAACTGGACG GCAAACGCCG GGACCAGTTT      180

GACATGATCG ACCGATTTAT CGCCGATTAC GCGATCAACG TTGAGCGCAC AGAGCAGGCA      240

ATGCGCCTGG AGGCGGTGGA AATAGCCCGT ATGTGGTGG ATATTCACGT CAGCCGGGAG       300

GAGATCATTG CCATCACTAC CGCCATCACG CCGGCCAAAG CGGTCGAGGT GATGGCGCAG      360

ATGAACGTGG TGGAGATGAT GATGGCGCTG CAGAAGATGC GTGCCCGCCG GACCCCCTCC      420

AACCAGTGCC ACGTCACCAA TCTCAAAGAT AATCCGGTGC AGATTGCCGC TGACGCCGCC      480

GAGGCCGGGA TCCGCGGCTT CTCAGAACAG GAGACCACGG TCGGTATCGC GCGCTACGCG      540

CCGTTTAACG CCCTGGCGCT GTTGGTCGGT TCGCAGTGCG GCCGCCCCGG CGTGTTGACG      600

CAGTGCTCGG TGGAAGAGGC CACCGAGCTG GAGCTGGGCA TGCGTGGCTT AACCAGCTAC      660

GCCGAGACGG TGTCGGTCTA CGGCACCGAA GCGGTATTTA CCGACGGCGA TGATACGCCG      720

TGGTCAAAGG CGTTCCTCGC CTCGGCCTAC GCCTCCCGCG GGTTGAAAAT GCGCTACACC      780

TCCGGCACCG GATCCGAAGC GCTGATGGGC TATTCGGAGA GCAAGTCGAT GCTCTACCTC      840

GAATCGCGCT GCATCTTCAT TACTAAAGGC GCCGGGGTTC AGGGACTGCA AAACGGCGCG      900

GTGAGCTGTA TCGGCATGAC CGGCGCTGTG CCGTCGGGCA TTCGGGCGGT GCTGGCGGAA      960

AACCTGATCG CCTCTATGCT CGACCTCGAA GTGGCGTCCG CCAACGACCA GACTTTCTCC     1020

CACTCGGATA TTCGCCGCAC CGCGCGCACC CTGATGCAGA TGCTGCCGGG CACCGACTTT     1080

ATTTTCTCCG GCTACAGCGC GGTGCCGAAC TACGACAACA TGTTCGCCGG CTCGAACTTC     1140

GATGCGGAAG ATTTTGATGA TTACAACATC CTGCAGCGTG ACCTGATGGT TGACGGCGGC     1200

CTGCGTCCGG TGACCGAGGC GGAAACCATT GCCATTCGCC AGAAAGCGGC GCGGGCGATC     1260

CAGGCGGTTT TCCGCGAGCT GGGGCTGCCG CCAATCGCCG ACGAGGAGGT GGAGGCCGCC     1320

ACCTACGCGC ACGGCAGCAA CGAGATGCCG CCGCGTAACG TGGTGGAGGA TCTGAGTGCG     1380
```

```
GTGGAAGAGA TGATGAAGCG CAACATCACC GGCCTCGATA TTGTCGGCGC GCTGAGCCGC    1440

AGCGGCTTTG AGGATATCGC CAGCAATATT CTCAATATGC TGCGCCAGCG GGTCACCGGC    1500

GATTACCTGC AGACCTCGGC CATTCTCGAT CGGCAGTTCG AGGTGGTGAG TGCGGTCAAC    1560

GACATCAATG ACTATCAGGG GCCGGGCACC GGCTATCGCA TCTCTGCCGA ACGCTGGGCG    1620

GAGATCAAAA ATATTCCGGG CGTGGTTCAG CCCGACACCA TTGAATAA                1668
```

(2) INFORMATION FOR SEQ ID NO:7:

(i) SEQUENCE CHARACTERISTICS:
        (A) LENGTH: 585 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
GTGCAACAGA CAACCCAAAT TCAGCCCTCT TTTACCCTGA AAACCCGCGA GGGCGGGGTA      60

GCTTCTGCCG ATGAACGCGC CGATGAAGTG GTGATCGGCG TCGGCCCTGC CTTCGATAAA     120

CACCAGCATC ACACTCTGAT CGATATGCCC CATGGCGCGA TCCTCAAAGA GCTGATTGCC     180

GGGGTGGAAG AAGAGGGGCT TCACGCCCGG GTGGTGCGCA TTCTGCGCAC GTCCGACGTC     240

TCCTTTATGG CCTGGGATGC GGCCAACCTG AGCGGCTCGG GGATCGGCAT CGGTATCCAG     300

TCGAAGGGGA CCACGGTCAT CCATCAGCGC GATCTGCTGC CGCTCAGCAA CCTGGAGCTG     360

TTCTCCCAGG CGCCGCTGCT GACGCTGGAG ACCTACCGGC AGATTGGCAA AAACGCTGCG     420

CGCTATGCGC GCAAAGAGTC ACCTTCGCCG GTGCCGGTGG TGAACGATCA GATGGTGCGG     480

CCGAAATTTA TGGCCAAAGC CGCGCTATTT CATATCAAAG AGACCAAACA TGTGGTGCAG     540

GACGCCGAGC CCGTCACCCT GCACATCGAC TTAGTAAGGG AGTGA                    585
```

(2) INFORMATION FOR SEQ ID NO:8:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
ATGAGCGAGA AAACCATGCG CGTGCAGGAT TATCCGTTAG CCACCCGCTG CCCGGAGCAT      60

ATCCTGACGC CTACCGGCAA ACCATTGACC GATATTACCC TCGAGAAGGT GCTCTCTGGC     120

GAGGTGGGCC CGCAGGATGT GCGGATCTCC CGCCAGACCC TTGAGTACCA GGCGCAGATT     180

GCCGAGCAGA TGCAGCGCCA TGCGGTGGCG CGCAATTTCC GCCGCGCGGC GGAGCTTATC     240

GCCATTCCTG ACGAGCGCAT TCTGGCTATC TATAACGCGC TGCGCCCGTT CCGCTCCTCG     300

CAGGCGGAGC TGCTGGCGAT CGCCGACGAG CTGGAGCACA CCTGGCATGC GACAGTGAAT     360

GCCGCCTTTG TCCGGGAGTC GGCGGAAGTG TATCAGCAGC GGCATAAGCT GCGTAAAGGA     420
```

AGCTAA                                                          426

(2) INFORMATION FOR SEQ ID NO:9:

(i) SEQUENCE CHARACTERISTICS:
        (A) LENGTH: 1164 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
ATGAGCTATC GTATGTTTGA TTATCTGGTG CCAAACGTTA ACTTTTTTGG CCCCAACGCC      60
ATTTCCGTAG TCGGCGAACG CTGCCAGCTG CTGGGGGGGA AAAAAGCCCT GCTGGTCACC     120
GACAAAGGCC TGCGGGCAAT TAAAGATGGC GCGGTGGACA AAACCCTGCA TTATCTGCGG     180
GAGGCCGGGA TCGAGGTGGC GATCTTTGAC GGCGTCGAGC CGAACCCGAA AGACACCAAC     240
GTGCGCGACG GCCTCGCCGT GTTTCGCCGC GAACAGTGCG ACATCATCGT CACCGTGGGC     300
GGCGGCAGCC CGCACGATTG CGGCAAAGGC ATCGGCATCG CCGCCACCCA TGAGGGCGAT     360
CTGTACCAGT ATGCCGGAAT CGAGACCCTG ACCAACCCGC TGCCGCCTAT CGTCGCGGTC     420
AATACCACCG CCGGCACCGC CAGCGAGGTC ACCCGCCACT GCGTCCTGAC CAACACCGAA     480
ACCAAAGTGA AGTTTGTGAT CGTCAGCTGG CGCAAACTGC CGTCGGTCTC TATCAACGAT     540
CCACTGCTGA TGATCGGTAA ACCGGCCGCC CTGACCGCGG CGACCGGGAT GGATGCCCTG     600
ACCCACGCCG TAGAGGCCTA TATCTCCAAA GACGCTAACC CGGTGACGGA CGCCGCCGCC     660
ATGCAGGCGA TCCGCCTCAT CGCCCGCAAC CTGCGCCAGG CCGTGGCCCT CGGCAGCAAT     720
CTGCAGGCGC GGGAAAACAT GGCCTATGCT TCTCTGCTGG CCGGGATGGC TTTCAATAAC     780
GCCAACCTCG GCTACGTGCA CGCCATGGCC CACCAGCTGG GCGGCCTGTA CGACATGCCG     840
CACGGCGTGG CCAACGCTGT CCTGCTGCCG CATGTGGCGC GCTACAACCT GATCGCCAAC     900
CCGGAGAAAT TCGCCGATAT CGCTGAACTG ATGGGCGAAA ATATCACCGG ACTGTCCACT     960
CTCGACGCGG CGGAAAAAGC CATCGCCGCT ATCACGCGTC TGTCGATGGA TATCGGTATT    1020
CCGCAGCATC TGCGCGATCT GGGGGTAAAA GAGGCCGACT TCCCCTACAT GGCGGAGATG    1080
GCTCTAAAAG ACGGCAATGC GTTCTCGAAC CCGCGTAAAG GCAACGAGCA GGAGATTGCC    1140
GCGATTTTCC GCCAGGCATT CTGA                                          1164
```

(2) INFORMATION FOR SEQ ID NO:10:

(i) SEQUENCE CHARACTERISTICS:
        (A) LENGTH: 12145 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
GTCGACCACC ACGGTGGTGA CTTTAATGCC GCTCTCATGC AGCAGCTCGG TGGCGGTCTC      60
AAAATTCAGG ATGTCGCCGG TATAGTTTTT GATAATCAGC AAGACGCCTT CGCCGCCGTC     120
```

```
AATTTGCATC GCGCATTCAA ACATTTTGTC CGGCGTCGGC GAGGTGAATA TTTCCCCCGG    180

ACAGGCGCCG GAGAGCATGC CCTGGCCGAT ATAGCCGCAG TGCATCGGTT CATGTCCGCT    240

GCCGCCGCCG GAGAGCAGGG CCACCTTGCC AGCCACCGGC GCGTCGGTGC GGGTCACATA    300

CAGCGGGTCC TGATGCAGGG TCAGCTGCGG ATGGGCTTTA GCCAGCCCCT GTAATTGTTC    360

ATTCAGTACA TCTTCAACAC GGTTAATCAG CTTTTTCATT ATTCAGTGCT CCGTTGGAGA    420

AGGTTCGATG CCGCCTCTCT GCTGGCGGAG GCGGTCATCG CGTAGGGGTA TCGTCTGACG    480

GTGGAGCGTG CCTGGCGATA TGATGATTCT GGCTGAGCGG ACGAAAAAAA GAATGCCCCG    540

ACGATCGGGT TTCATTACGA AACATTGCTT CCTGATTTTG TTTCTTTATG GAACGTTTTT    600

GCTGAGGATA TGGTGAAAAT GCGAGCTGGC GCGCTTTTTT TCTTCTGCCA TAAGCGGCGG    660

TCAGGATAGC CGGCGAAGCG GGTGGGAAAA AATTTTTTGC TGATTTTCTG CCGACTGCGG    720

GAGAAAAGGC GGTCAAACAC GGAGGATTGT AAGGGCATTA TGCGGCAAAG GAGCGGATCG    780

GGATCGCAAT CCTGACAGAG ACTAGGGTTT TTTGTTCCAA TATGGAACGT AAAAAATTAA    840

CCTGTGTTTC ATATCAGAAC AAAAAGGCGA AGATTTTTT TGTTCCCTGC CGGCCCTACA    900

GTGATCGCAC TGCTCCGGTA CGCTCCGTTC AGGCCGCGCT TCACTGGCCG GCGCGGATAA    960

CGCCAGGGCT CATCATGTCT ACATGCGCAC TTATTTGAGG GTGAAAGGAA TGCTAAAAGT   1020

TATTCAATCT CCAGCCAAAT ATCTTCAGGG TCCTGATGCT GCTGTTCTGT TCGGTCAATA   1080

TGCCAAAAAC CTGGCGGAGA GCTTCTTCGT CATCGCTGAC GATTTCGTAA TGAAGCTGGC   1140

GGGAGAGAAA GTGGTGAATG GCCTGCAGAG CCACGATATT CGCTGCCATG CGGAACGGTT   1200

TAACGGCGAA TGCAGCCATG CGGAAATCAA CCGTCTGATG GCGATTTTGC AAAAACAGGG   1260

CTGCCGCGGC GTGGTCGGGA TCGGCGGTGG TAAAACCCTC GATACCGCGA AGGCGATCGG   1320

TTACTACCAG AAGCTGCCGG TGGTGGTGAT CCCGACCATC GCCTCGACCG ATGCGCCAAC   1380

CAGCGCGCTG TCGGTGATCT ACACCGAAGC GGGCGAGTTT GAAGAGTATC TGATCTATCC   1440

GAAAAACCCG GATATGGTGG TGATGGACAC GGCGATTATC GCCAAAGCGC CGGTACGCCT   1500

GCTGGTCTCC GGCATGGGCG ATGCGCTCTC CACCTGGTTC GAGGCCAAAG CTTGCTACGA   1560

TGCGCGCGCC ACCAGCATGG CCGGAGGACA GTCCACCGAG GCGGCGCTGA GCCTCGCCCG   1620

CCTGTGCTAT GATACGCTGC TGGCGGAGGG CGAAAAGGCC CGTCTGGCGG CGCAGGCCGG   1680

GGTAGTGACC GAAGCGCTGG AGCGCATCAT CGAGGCGAAC ACTTACCTCA GCGGCATTGG   1740

CTTTGAAAGC AGTGGCCTGG CCGCTGCCCA TGCAATCCAC AACGGTTTCA CCATTCTTGA   1800

AGAGTGCCAT CACCTGTATC ACGGTGAGAA AGTGGCCTTC GGTACCCTGG CGCAGCTGGT   1860

GCTGCAGAAC AGCCCGATGG ACGAGATTGA AACGGTGCAG GGCTTCTGCC AGCGCGTCGG   1920

CCTGCCGGTG ACGCTCGCGC AGATGGGCGT CAAAGAGGGG ATCGACGAGA AAATCGCCGC   1980

GGTGGCGAAA GCTACCTGCG CGGAAGGGGA AACCATCCAT AATATGCCGT TTGCGGTGAC   2040

CCCGGAGAGC GTCCATGCCG CTATCCTCAC CGCCGATCTG TTAGGCCAGC AGTGGCTGGC   2100

GCGTTAATTC GCGGTGGCTA AACCGCTGGC CCAGGTCAGC GGTTTTTCTT TCTCCCCTCC   2160

GGCAGTCGCT GCCGGAGGGG TTCTCTATGG TACAACGCGG AAAAGGATAT GACTGTTCAG   2220

ACTCAGGATA CCGGGAAGGC GGTCTCTTCC GTCATTGCCC AGTCATGGCA CCGCTGCAGC   2280

AAGTTTATGC AGCGCGAAAC CTGGCAAACG CCGCACCAGG CCCAGGGCCT GACCTTCGAC   2340

TCCATCTGTC GGCGTAAAAC CGCGCTGCTC ACCATCGGCC AGGCGGCGCT GGAAGACGCC   2400

TGGGAGTTTA TGGACGGCCG CCCCTGCGCG CTGTTTATTC TTGATGAGTC CGCCTGCATC   2460
```

-continued

```
CTGAGCCGTT GCGGCGAGCC GCAAACCCTG GCCCAGCTGG CTGCCCTGGG ATTTCGCGAC    2520

GGCAGCTATT GTGCGGAGAG CATTATCGGC ACCTGCGCGC TGTCGCTGGC CGCGATGCAG    2580

GGCCAGCCGA TCAACACCGC CGGCGATCGG CATTTTAAGC AGGCGCTACA GCCATGGAGT    2640

TTTTGCTCGA CGCCGGTGTT TGATAACCAC GGGCGGCTGT TCGGCTCTAT CTCGCTTTGC    2700

TGTCTGGTCG AGCACCAGTC CAGCGCCGAC CTCTCCCTGA CGCTGGCCAT CGCCCGCGAG    2760

GTGGGTAACT CCCTGCTTAC CGACAGCCTG CTGGCGGAAT CCAACCGTCA CCTCAATCAG    2820

ATGTACGGCC TGCTGGAGAG CATGGACGAT GGGGTGATGG CGTGGAACGA ACAGGGCGTG    2880

CTGCAGTTTC TCAATGTTCA GGCGGCGAGA CTGCTGCATC TTGATGCTCA GGCCAGCCAG    2940

GGGAAAAATA TCGCCGATCT GGTGACCCTC CCGGCGCTGC TGCGCCGCGC CATCAAACAC    3000

GCCCGCGGCC TGAATCACGT CGAAGTCACC TTTGAAAGTC AGCATCAGTT TGTCGATGCG    3060

GTGATCACCT TAAAACCGAT TGTCGAGGCG CAAGGCAACA GTTTTATTCT GCTGCTGCAT    3120

CCGGTGGAGC AGATGCGGCA GCTGATGACC AGCCAGCTCG GTAAAGTCAG CCACACCTTT    3180

GAGCAGATGT CTGCCGACGA TCCGGAAACC CGACGCCTGA TCCACTTTGG CCGCCAGGCG    3240

GCGCGCGGCG GCTTCCCGGT GCTACTGTGC GGCGAAGAGG GGGTCGGGAA AGAGCTGCTG    3300

AGCCAGGCTA TTCACAATGA AAGCGAACGG GCGGGCGGCC CCTACATCTC CGTCAACTGC    3360

CAGCTATATG CCGACAGCGT GCTGGGCCAG GACTTTATGG GCAGCGCCCC TACCGACGAT    3420

GAAAATGGTC GCCTGAGCCG CCTTGAGCTG GCCAACGGCG GCACCCTGTT TCTGGAAAAG    3480

ATCGAGTATC TGGCGCCGGA GCTGCAGTCG GCTCTGCTGC AGGTGATTAA GCAGGGCGTG    3540

CTCACCCGCC TCGACGCCCG GCGCCTGATC CCGGTGGATG TGAAGGTGAT TGCCACCACC    3600

ACCGTCGATC TGGCCAATCT GGTGGAACAG AACCGCTTTA GCCGCCAGCT GTACTATGCG    3660

CTGCACTCCT TTGAGATCGT CATCCCGCCG CTGCGCGCCC GACGCAACAG TATTCCGTCG    3720

CTGGTGCATA ACCGGTTGAA GAGCCTGGAG AAGCGTTTCT CTTCGCGACT GAAAGTGGAC    3780

GATGACGCGC TGGCACAGCT GGTGGCCTAC TCGTGGCCGG GGAATGATTT TGAGCTCAAC    3840

AGCGTCATTG AGAATATCGC CATCAGCAGC GACAACGGCC ACATTCGCCT GAGTAATCTG    3900

CCGGAATATC TCTTTTCCGA GCGGCCGGGC GGGGATAGCG CGTCATCGCT GCTGCCGGCC    3960

AGCCTGACTT TTAGCGCCAT CGAAAAGGAA GCTATTATTC ACGCCGCCCG GGTGACCAGC    4020

GGGCGGGTGC AGGAGATGTC GCAGCTGCTC AATATCGGCC GCACCACCCT GTGGCGCAAA    4080

ATGAAGCAGT ACGATATTGA CGCCAGCCAG TTCAAGCGCA AGCATCAGGC CTAGTCTCTT    4140

CGATTCGCGC CATGGAGAAC AGGGCATCCG ACAGGCGATT GCTGTAGCGT TGAGCGCGT    4200

CGCGCAGCGG ATGCGCGCGG TCCATGGCCG TCAGCAGGCG TTCGAGCCGA CGGGACTGGG    4260

TGCGCGCCAC GTGCAGCTGG GCAGAGGCGA GATTCCTCCC CGGGATCACG AACTGTTTTA    4320

ACGGCCGCT CTCGGCCATA TTGCGGTCGA TAAGCCGCTC CAGGGCGGTG ATCTCCTCTT    4380

CGCCGATCGT CTGGCTCAGG CGGGTCAGGC CCCGCGCATC GCTGGCCAGT TCAGCCCCCA    4440

GCACGAACAG CGTCTGCTGA ATATGGTGCA GGCTTTCCCG CAGCCCGGCG TCGCGGGTCG    4500

TGGCGTAGCA GACGCCCAGC TGGGATATCA GTTCATCGAC GGTGCCGTAG GCCTCGACGC    4560

GAATATGGTC TTTCTCGATG CGGCTGCCGC CGTACAGGGC GGTGGTGCCT TTATCCCCGG    4620

TGCGGGTATA GATACGATAC ATTCAGTTTC TCTCACTTAA CGGCAGGACT TTAACCAGCT    4680

GCCCGGCGTT GGCGCCAGCG GTACGCAGTT GATCGTCGCT ATCGGTGACG TGTCCGGTAG    4740

CCAGCGGCGC GTCCGCCGGC AGCTGGGCAT GAGTGAGGGC TATCTCGCCG GACGCGCTGA    4800

GCCCGATACC CACCCGCAGG GGCGAGCTTC TGGCCGCCAG GGCGCCCAGC GCAGCGGCGT    4860
```

-continued

```
CACCGCCTCC GTCATAGGTT ATGGTCTGGC AGGGGACCCC CTGCTCCTCC AGCCCCCAGC    4920

ACAGCTCATT GATGGCGCCG GCATGGTGCC CGCGCGGATC GTAAAACAGG CGTACGCCTG    4980

GCGGTGAAAG CGACATGACG GTCCCCTCGT TAACACTCAG AATGCCTGGC GGAAAATCGC    5040

GGCAATCTCC TGCTCGTTGC CTTTACGCGG GTTCGAGAAC GCATTGCCGT CTTTTAGAGC    5100

CATCTCCGCC ATGTAGGGGA AGTCGGCCTC TTTTACCCCC AGATCGCGCA GATGCTGCGG    5160

AATACCGATA TCCATCGACA GACGCGTGAT AGCGGCGATG GCTTTTTCCG CCGCGTCGAG    5220

AGTGGACAGT CCGGTGATAT TTTCGCCCAT CAGTTCAGCG ATATCGGCGA ATTTCTCCGG    5280

GTTGGCGATC AGGTTGTAGC GCGCCACATG CGGCAGCAGG ACAGCGTTGG CCACGCCGTG    5340

CGGCATGTCG TACAGGCCGC CCAGCTGGTG CGCCATGGCG TGCACGTAGC CGAGGTTGGC    5400

GTTATTGAAA GCCATCCCGG CCAGCAGAGA AGCATAGGCC ATGTTTTCCC GCGCCTGCAG    5460

ATTGCTGCCG AGGGCCACGG CCTGGCGCAG GTTGCGGGCG ATGAGGCGGA TCGCCTGCAT    5520

GGCGGCGGCG TCCGTCACCG GGTTAGCGTC TTTGGAGATA TAGGCCTCTA CGGCGTGGGT    5580

CAGGGCATCC ATCCCGGTCG CCGCGGTCAG GGCGGCCGGT TTACCGATCA TCAGCAGTGG    5640

ATCGTTGATA GAGACCGACG GCAGTTTGCG CCAGCTGACG ATCACAAACT TCACTTTGGT    5700

TTCGGTGTTG GTCAGGACGC AGTGGCGGGT GACCTCGCTG GCGGTGCCGG CGGTGGTATT    5760

GACCGCGACG ATAGGCGGCA GCGGGTTGGT CAGGGTCTCG ATTCCGGCAT ACTGGTACAG    5820

ATCGCCCTCA TGGGTGGCGG CGATGCCGAT GCCTTTGCCG CAATCGTGCG GGCTGCCGCC    5880

GCCCACGGTG ACGATGATGT CGCACTGTTC GCGGCGAAAC ACGGCGAGGC CGTCGCGCAC    5940

GTTGGTGTCT TCGGGTTCG GCTCGACGCC GTCAAAGATC GCCACCTCGA TCCCGGCCTC    6000

CCGCAGATAA TGCAGGGTTT TGTCCACCGC GCCATCTTTA ATTGCCCGCA GGCCTTTGTC    6060

GGTGACCAGC AGGGCTTTTT TCCCCCCCAG CAGCTGGCAG CGTTCGCCGA CTACGGAAAT    6120

GGCGTTGGGG CCAAAAAAGT TAACGTTTGG CACCAGATAA TCAAACATAC GATAGCTCAT    6180

AATATACCTT CTCGCTTCAG GTTATAATGC GGAAAAACAA TCCAGGGCGC ACTGGGCTAA    6240

TAATTGATCC TGCTCGACCG TACCGCCGCT AACGCCGACG GCGCCAATTA CCTGCTCATT    6300

AAAAATAACT GGCAGGCCGC CGCCAAAAAT AATAATTCGC TGTTGGTTGG TTAGCTGCAG    6360

ACCGTACAGA GATTGTCCTG GCTGGACCGC TGACGTAATT TCATGGGTAC CTTGCTTCAG    6420

GCTGCAGGCG CTCCAGGCTT TATTCAGGGA AATATCGCAG CTGGAGACGA AGGCCTCGTC    6480

CATCCGCTGG ATAAGCAGCG TGTTGCCTCC GCGGTCAACT ACGGAAAACA CCACCGCCAC    6540

GTTGATCTCA GTGGCTTTTT TTTCCACCGC CGCCGCCATT TGCTGGGCGG CGGCCAGGGT    6600

GATTGTCTGA ACTTGTTGGC TCTTGTTCAT CATTCTCTCC CGCACCAGGA TAACGCTGGC    6660

GCGAATAGTC AGTAGGGGGC GATAGTAAAA AACTATTACC ATTCGGTTGG CTTGCTTTAT    6720

TTTTGTCAGC GTTATTTTGT CGCCCGCCAT GATTTAGTCA ATAGGGTTAA AATAGCGTCG    6780

GAAAAACGTA ATTAAGGGCG TTTTTTATTA ATTGATTTAT ATCATTGCGG GCGATCACAT    6840

TTTTTATTTT TGCCGCCGGA GTAAAGTTTC ATAGTGAAAC TGTCGGTAGA TTTCGTGTGC    6900

CAAATTGAAA CGAAATTAAA TTTATTTTTT TCACCACTGG CTCATTTAAA GTTCCGCTAT    6960

TGCCGGTAAT GGCCGGGCGG CAACGACGCT GGCCCGGCGT ATTCGCTACC GTCTGCGGAT    7020

TTCACCTTTT GAGCCGATGA ACAATGAAAA GATCAAAACG ATTTGCAGTA CTGGCCCAGC    7080

GCCCCGTCAA TCAGGACGGG CTGATTGGCG AGTGGCCTGA AGAGGGGCTG ATCGCCATGG    7140

ACAGCCCCTT TGACCCGGTC TCTTCAGTAA AAGTGGACAA CGGTCTGATC GTCGAACTGG    7200
```

```
ACGGCAAACG CCGGGACCAG TTTGACATGA TCGACCGATT TATCGCCGAT TACGCGATCA    7260

ACGTTGAGCG CACAGAGCAG GCAATGCGCC TGGAGGCGGT GGAAATAGCC CGTATGCTGG    7320

TGGATATTCA CGTCAGCCGG GAGGAGATCA TTGCCATCAC TACCGCCATC ACGCCGGCCA    7380

AAGCGGTCGA GGTGATGGCG CAGATGAACG TGGTGGAGAT GATGATGGCG CTGCAGAAGA    7440

TGCGTGCCCG CCGGACCCCC TCCAACCAGT GCCACGTCAC CAATCTCAAA GATAATCCGG    7500

TGCAGATTGC CGCTGACGCC GCCGAGGCCG GGATCCGCGG CTTCTCAGAA CAGGAGACCA    7560

CGGTCGGTAT CGCGCGCTAC GCGCCGTTTA ACGCCCTGGC GCTGTTGGTC GGTTCGCAGT    7620

GCGGCCGCCC CGGCGTGTTG ACGCAGTGCT CGGTGGAAGA GGCCACCGAG CTGGAGCTGG    7680

GCATGCGTGG CTTAACCAGC TACGCCGAGA CGGTGTCGGT CTACGGCACC GAAGCGGTAT    7740

TTACCGACGG CGATGATACG CCGTGGTCAA AGGCGTTCCT CGCCTCGGCC TACGCCTCCC    7800

GCGGGTTGAA AATGCGCTAC ACCTCCGGCA CCGGATCCGA AGCGCTGATG GGCTATTCGG    7860

AGAGCAAGTC GATGCTCTAC CTCGAATCGC GCTGCATCTT CATTACTAAA GGCGCCGGGG    7920

TTCAGGGACT GCAAAACGGC GCGGTGAGCT GTATCGGCAT GACCGGCGCT GTGCCGTCGG    7980

GCATTCGGGC GGTGCTGGCG GAAAACCTGA TCGCCTCTAT GCTCGACCTC GAAGTGGCGT    8040

CCGCCAACGA CCAGACTTTC TCCCACTCGG ATATTCGCCG CACCGCGCGC ACCCTGATGC    8100

AGATGCTGCC GGGCACCGAC TTTATTTTCT CCGGCTACAG CGCGGTGCCG AACTACGACA    8160

ACATGTTCGC CGGCTCGAAC TTCGATGCGG AAGATTTTGA TGATTACAAC ATCCTGCAGC    8220

GTGACCTGAT GGTTGACGGC GGCCTGCGTC CGGTGACCGA GGCGGAAACC ATTGCCATTC    8280

GCCAGAAAGC GGCGCGGGCG ATCCAGGCGG TTTTCCGCGA GCTGGGGCTG CCGCCAATCG    8340

CCGACGAGGA GGTGGAGGCC GCCACCTACG CGCACGGCAG CAACGAGATG CCGCCGCGTA    8400

ACGTGGTGGA GGATCTGAGT GCGGTGGAAG AGATGATGAA GCGCAACATC ACCGGCCTCG    8460

ATATTGTCGG CGCGCTGAGC CGCAGCGGCT TTGAGGATAT CGCCAGCAAT ATTCTCAATA    8520

TGCTGCGCCA GCGGGTCACC GGCGATTACC TGCAGACCTC GGCCATTCTC GATCGGCAGT    8580

TCGAGGTGGT GAGTGCGGTC AACGACATCA ATGACTATCA GGGGCCGGGC ACCGGCTATC    8640

GCATCTCTGC CGAACGCTGG GCGGAGATCA AAAATATTCC GGGCGTGGTT CAGCCCGACA    8700

CCATTGAATA AGGCGGTATT CCTGTGCAAC AGACAACCCA AATTCAGCCC TCTTTTACCC    8760

TGAAAACCCG CGAGGGCGGG GTAGCTTCTG CCGATGAACG CGCCGATGAA GTGGTGATCG    8820

GCGTCGGCCC TGCCTTCGAT AAACACCAGC ATCACACTCT GATCGATATG CCCCATGGCG    8880

CGATCCTCAA AGAGCTGATT GCCGGGGTGG AAGAAGAGGG GCTTCACGCC CGGGTGGTGC    8940

GCATTCTGCG CACGTCCGAC GTCTCCTTTA TGGCCTGGGA TGCGGCCAAC CTGAGCGGCT    9000

CGGGGATCGG CATCGGTATC CAGTCGAAGG GGACCACGGT CATCCATCAG CGCGATCTGC    9060

TGCCGCTCAG CAACCTGGAG CTGTTCTCCC AGGCGCCGCT GCTGACGCTG GAGACCTACC    9120

GGCAGATTGG CAAAAACGCT GCGCGCTATG CGCGCAAAGA GTCACCTTCG CCGGTGCCGG    9180

TGGTGAACGA TCAGATGGTG CGGCCGAAAT TTATGGCCAA AGCCGCGCTA TTTCATATCA    9240

AAGAGACCAA ACATGTGGTG CAGGACGCCG AGCCCGTCAC CCTGCACATC GACTTAGTAA    9300

GGGAGTGACC ATGAGCGAGA AAACCATGCG CGTGCAGGAT TATCCGTTAG CCACCCGCTG    9360

CCCCGGAGCAT ATCCTGACGC CTACCGGCAA ACCATTGACC GATATTACCC TCGAGAAGGT    9420

GCTCTCTGGC GAGGTGGGCC CGCAGGATGT GCGGATCTCC CGCCAGACCC TTGAGTACCA    9480

GGCGCAGATT GCCGAGCAGA TGCAGCGCCA TGCGGTGGCG CGCAATTTCC GCCGCGCGGC    9540

GGAGCTTATC GCCATTCCTG ACGAGCGCAT TCTGGCTATC TATAACGCGC TGCGCCCGTT    9600
```

```
CCGCTCCTCG CAGGCGGAGC TGCTGGCGAT CGCCGACGAG CTGGAGCACA CCTGGCATGC    9660

GACAGTGAAT GCCGCCTTTG TCCGGGAGTC GGCGGAAGTG TATCAGCAGC GGCATAAGCT    9720

GCGTAAAGGA AGCTAAGCGG AGGTCAGCAT GCCGTTAATA GCCGGGATTG ATATCGGCAA    9780

CGCCACCACC GAGGTGGCGC TGGCGTCCGA CTACCCGCAG GCGAGGGCGT TTGTTGCCAG    9840

CGGGATCGTC GCGACGACGG GCATGAAAGG GACGCGGGAC AATATCGCCG GGACCCTCGC    9900

CGCGCTGGAG CAGGCCCTGG CGAAAACACC GTGGTCGATG AGCGATGTCT CTCGCATCTA    9960

TCTTAACGAA GCCGCGCCGG TGATTGGCGA TGTGGCGATG GAGACCATCA CCGAGACCAT   10020

TATCACCGAA TCGACCATGA TCGGTCATAA CCCGCAGACG CCGGGCGGGG TGGGCGTTGG   10080

CGTGGGGACG ACTATCGCCC TCGGGCGGCT GGCGACGCTG CCGGCGGCGC AGTATGCCGA   10140

GGGGTGGATC GTACTGATTG ACGACGCCGT CGATTTCCTT GACGCCGTGT GGTGGCTCAA   10200

TGAGGCGCTC GACCGGGGGA TCAACGTGGT GGCGGCGATC CTCAAAAAGG ACGACGGCGT   10260

GCTGGTGAAC AACCGCCTGC GTAAAACCCT GCCGGTGGTG GATGAAGTGA CGCTGCTGGA   10320

GCAGGTCCCC GAGGGGGTAA TGGCGGCGGT GGAAGTGGCC GCGCCGGGCC AGGTGGTGCG   10380

GATCCTGTCG AATCCCTACG GGATCGCCAC CTTCTTCGGG CTAAGCCCGG AAGAGACCCA   10440

GGCCATCGTC CCCATCGCCC GCGCCCTGAT TGGCAACCGT TCCGCGGTGG TGCTCAAGAC   10500

CCCGCAGGGG GATGTGCAGT CGCGGGTGAT CCCGGCGGGC AACCTCTACA TTAGCGGCGA   10560

AAAGCGCCGC GGAGAGGCCG ATGTCGCCGA GGGCGCGGAA GCCATCATGC AGGCGATGAG   10620

CGCCTGCGCT CCGGTACGCG ACATCCGCGG CGAACCGGGC ACCCACGCCG GCGGCATGCT   10680

TGAGCGGGTG CGCAAGGTAA TGGCGTCCCT GACCGGCCAT GAGATGAGCG CGATATACAT   10740

CCAGGATCTG CTGGCGGTGG ATACGTTTAT TCCGCGCAAG GTGCAGGGCG GGATGGCCGG   10800

CGAGTGCGCC ATGGAGAATG CCGTCGGGAT GGCGGCGATG GTGAAAGCGG ATCGTCTGCA   10860

AATGCAGGTT ATCGCCCGCG AACTGAGCGC CCGACTGCAG ACCGAGGTGG TGGTGGGCGG   10920

CGTGGAGGCC AACATGGCCA TCGCCGGGGC GTTAACCACT CCCGGCTGTG CGGCGCCGCT   10980

GGCGATCCTC GACCTCGGCG CCGGCTCGAC GGATGCGGCG ATCGTCAACG CGGAGGGGCA   11040

GATAACGGCG GTCCATCTCG CCGGGGCGGG GAATATGGTC AGCCTGTTGA TTAAAACCGA   11100

GCTGGGCCTC GAGGATCTTT CGCTGGCGGA AGCGATAAAA AAATACCCGC TGGCCAAAGT   11160

GGAAAGCCTG TTCAGTATTC GTCACGAGAA TGGCGCGGTG GAGTTCTTTC GGGAAGCCCT   11220

CAGCCCGGCG GTGTTCGCCA AGTGGTGTA CATCAAGGAG GGCGAACTGG TGCCGATCGA   11280

TAACGCCAGC CCGCTGGAAA AAATTCGTCT CGTGCGCCGG CAGGCGAAAG AGAAAGTGTT   11340

TGTCACCAAC TGCCTGCGCG CGCTGCGCCA GGTCTCACCC GGCGGTTCCA TTCGCGATAT   11400

CGCCTTTGTG GTGCTGGTGG GCGGCTCATC GCTGGACTTT GAGATCCCGC AGCTTATCAC   11460

GGAAGCCTTG TCGCACTATG GCGTGGTCGC CGGGCAGGGC AATATTCGGG GAACAGAAGG   11520

GCCGCGCAAT GCGGTCGCCA CCGGGCTGCT ACTGGCCGGT CAGGCGAATT AAACGGGCGC   11580

TCGCGCCAGC CTCTCTCTTT AACGTGCTAT TTCAGGATGC CGATAATGAA CCAGACTTCT   11640

ACCTTAACCG GGCAGTGCGT GGCCGAGTTT CTTGGCACCG GATTGCTCAT TTTCTTCGGC   11700

GCGGGCTGCG TCGCTGCGCT GCGGGTCGCC GGGGCCAGCT TTGGTCAGTG GGAGATCAGT   11760

ATTATCTGGG GCCTTGGCGT CGCCATGGCC ATCTACCTGA CGGCCGGTGT CTCCGGCGCG   11820

CACCTAAATC CGGCGGTGAC CATTGCCCTG TGGCTGTTCG CCTGTTTTGA ACGCCGCAAG   11880

GTGCTGCCGT TTATTGTTGC CCAGACGGCC GGGGCCTTCT GCGCCGCCGC GCTGGTGTAT   11940
```

```
GGGCTCTATC GCCAGCTGTT TCTCGATCTT GAACAGAGTC AGCATATCGT GCGCGGCACT    12000

GCCGCCAGTC TTAACCTGGC CGGGGTCTTT TCCACGTACC CGCATCCACA TATCACTTTT    12060

ATACAAGCGT TTGCCGTGGA GACCACCATC ACGGCAATCC TGATGGCGAT GATCATGGCC    12120

CTGACCGACG ACGGCAACGG AATTC                                          12145
```

(2) INFORMATION FOR SEQ ID NO:11:

(i) SEQUENCE CHARACTERISTICS:
        (A) LENGTH: 94 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

```
AGCTTAGGAG TCTAGAATAT TGAGCTCGAA TTCCCGGGCA TGCGGTACCG GATCCAGAAA    60

AAAGCCCGCA CCTGACAGTG CGGGCTTTTT TTTT                                94
```

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:12:

```
GGAATTCAGA TCTCAGCAAT GAGCGAGAAA ACCATGC                             37
```

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:13:

```
GCTCTAGATT AGCTTCCTTT ACGCAGC                                        27
```

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "PRIMER"

(iii) HYPOTHETICAL: NO (iv) ANTI-SENSE: NO (xi) SEQUENCE DESCRIPTION: SEQ ID NO:14:

GGCCAAGCTT AAGGAGGTTA ATTAAATGAA AAG                                33

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:15:

GCTCTAGATT ATTCAATGGT GTCGGG                                        26

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:16:

GCGCCGTCTA GAATTATGAG CTATCGTATG TTTGATTATC TG                      42

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (xi) SEQUENCE DESCRIPTION: SEQ ID NO:17:

TCTGATACGG GATCCTCAGA ATGCCTGGCG GAAAAT                             36

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "PRIMER"

(iii) HYPOTHETICAL: NO (iv) ANTI-SENSE: NO (xi) SEQUENCE DESCRIPTION: SEQ ID NO:18:

TCTATTGTGG ATGCTTTACC ATGGTTAAAA                                         30

(2) INFORMATION FOR SEQ ID NO:19:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (xi) SEQUENCE DESCRIPTION: SEQ ID NO:19:

CACCGACGCC GGATCCAAAC ACCAGC                                             26

(2) INFORMATION FOR SEQ ID NO:20:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (xi) SEQUENCE DESCRIPTION: SEQ ID NO:20:

TCACTGTCGA AGAGGATCCG TAAAATCAAC GCCATGAC                                38

(2) INFORMATION FOR SEQ ID NO:21:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (xi) SEQUENCE DESCRIPTION: SEQ ID NO:21:

GGCATTTGGC GGCGAAGCTT TATGGTGGCT ACAC                                    34

(2) INFORMATION FOR SEQ ID NO:22:

(i) SEQUENCE CHARACTERISTICS:
             (A) LENGTH: 18 base pairs
             (B) TYPE: nucleic acid
             (C) STRANDEDNESS: single
             (D) TOPOLOGY: linear
```

(ii) MOLECULE TYPE: other nucleic acid
            (A) DESCRIPTION: /desc = "PRIMER"

(iii) HYPOTHETICAL: NO (iv) ANTI-SENSE: NO (xi) SEQUENCE DESCRIPTION: SEQ ID NO:22:

TCGACGAATT CAGGAGGA                                                          18

(2) INFORMATION FOR SEQ ID NO:23:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (xi) SEQUENCE DESCRIPTION: SEQ ID NO:23:

CTAGTCCTCC TGAATTCG                                                          18

(2) INFORMATION FOR SEQ ID NO:24:

(i) SEQUENCE CHARACTERISTICS:
             (A) LENGTH: 4549 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

AGCTCGTCAG CGGGTGTTGG CGGGTGTCGG GGCTGGCTTA ACTATGCGGC ATCAGAGCAG      60

ATTGTACTGA GAGTGCACCA TATGCGGTGT GAAATACCGC ACAGATGCGT AAGGAGAAAA     120

TACCGCATCA GGCGCCATTC GCCATTCAGG CTGCGCAACT GTTGGGAAGG GCGATCGGTG     180

CGGGCCTCTT CGCTATTACG CCAGCTGGCG AAAGGGGGAT GTGCTGCAAG GCGATTAAGT     240

TGGGTAACGC CAGGGTTTTC CCAGTCACGA CGTTGTAAAA CGACGGCCAG TGAATTCGAG     300

CTCGGTACCC GGGGATCCTC TAGAGTCGAC CTGCAGGCAT GCAAGCTTGG CGTAATCATG     360

GTCATAGCTG TTTCCTGTGT GAAATTGTTA TCCGCTCACA ATTCCACACA ACATACGAGC     420

CGGAAGCATA AAGTGTAAAG CCTGGGGTGC CTAATGAGTG AGCTAACTCA CATTAATTGC     480

GTTGCGCTCA CTGCCCGCTT TCCAGTCGGG AAACCTGTCG TGCCAGCTGC ATTAATGAAT     540

CGGCCAACGC GAATTCCCGA CAGTAAGACG GGTAAGCCTG TTGATGATAC CGCTGCCTTA     600

CTGGGTGCAT TAGCCAGTCT GAATGACCTG TCACGGGATA ATCCGAAGTG GTCAGACTGG     660

AAAATCAGAG GGCAGGAACT GCTGAACAGC AAAAAGTCAG ATAGCACCAC ATAGCAGACC     720

CGCCATAAAA CGCCCTGAGA AGCCCGTGAC GGGCTTTTCT TGTATTATGG GTAGTTTCCT     780

TGCATGAATC CATAAAAGGC GCCTGTAGTG CCATTTACCC CCATTCACTG CCAGAGCCGT     840

GAGCGCAGCG AACTGAATGT CACGAAAAAG ACAGCGACTC AGGTGCCTGA TGGTCGGAGA     900

CAAAAGGAAT ATTCAGCGAT TTGCCCGAGC TTGCGAGGGT GCTACTTAAG CCTTTAGGGT     960

```
TTTAAGGTCT GTTTTGTAGA GGAGCAAACA GCGTTTGCGA CATCCTTTTG TAATACTGCG    1020

GAACTGACTA AAGTAGTGAG TTATACACAG GGCTGGGATC TATTCTTTTT ATCTTTTTTT    1080

ATTCTTTCTT TATTCTATAA ATTATAACCA CTTGAATATA AACAAAAAAA ACACACAAAG    1140

GTCTAGCGGA ATTTACAGAG GGTCTAGCAG AATTTACAAG TTTTCCAGCA AAGGTCTAGC    1200

AGAATTTACA GATACCCACA ACTCAAAGGA AAAGGACTAG TAATTATCAT TGACTAGCCC    1260

ATCTCAATTG GTATAGTGAT TAAAATCACC TAGACCAATT GAGATGTATG TCTGAATTAG    1320

TTGTTTTCAA AGCAAATGAA CTAGCGATTA GTCGCTATGA CTTAACGAG CATGAAACCA     1380

AGCTAATTTT ATGCTGTGTG GCACTACTCA ACCCCACGAT TGAAAACCCT ACAAGGAAAG    1440

AACGGACGGT ATCGTTCACT TATAACCAAT ACGCTCAGAT GATGAACATC AGTAGGGAAA    1500

ATGCTTATGG TGTATTAGCT AAAGCAACCA GAGAGCTGAT GACGAGAACT GTGGAAATCA    1560

GGAATCCTTT GGTTAAAGGC TTTGAGATTT CCAGTGGAC AAACTATGCC AAGTTCTCAA     1620

GCGAAAAATT AGAATTAGTT TTTAGTGAAG AGATATTGCC TTATCTTTTC CAGTTAAAAA    1680

AATTCATAAA ATATAATCTG GAACATGTTA AGTCTTTTGA AAACAAATAC TCTATGAGGA    1740

TTTATGAGTG GTTATTAAAA GAACTAACAC AAAAGAAAAC TCACAAGGCA AATATAGAGA    1800

TTAGCCTTGA TGAATTTAAG TTCATGTTAA TGCTTGAAAA TAACTACCAT GAGTTTAAAA    1860

GGCTTAACCA ATGGGTTTTG AAACCAATAA GTAAAGATTT AAACACTTAC AGCAATATGA    1920

AATTGGTGGT TGATAAGCGA GGCCGCCCGA CTGATACGTT GATTTCCAA GTTGAACTAG     1980

ATAGACAAAT GGATCTCGTA ACCGAACTTG AGAACAACCA GATAAAAATG AATGGTGACA    2040

AAATACCAAC AACCATTACA TCAGATTCCT ACCTACATAA CGGACTAAGA AAAACACTAC    2100

ACGATGCTTT AACTGCAAAA ATTCAGCTCA CCAGTTTTGA GGCAAAATTT TGAGTGACA     2160

TGCAAAGTAA GTATGATCTC AATGGTTCGT TCTCATGGCT CACGCAAAAA CAACGAACCA    2220

CACTAGAGAA CATACTGGCT AAATACGGAA GGATCTGAGG TTCTTATGGC TCTTGTATCT    2280

ATCAGTGAAG CATCAAGACT AACAAACAAA GTAGAACAA CTGTTCACCG TTACATATCA     2340

AAGGGAAAAC TGTCCATATG CACAGATGAA AACGGTGTAA AAAAGATAGA TACATCAGAG    2400

CTTTTACGAG TTTTTGGTGC ATTCAAAGCT GTTCACCATG AACAGATCGA CAATGTAACA    2460

GATGAACAGC ATGTAACACC TAATAGAACA GGTGAAACCA GTAAAACAAA GCAACTAGAA    2520

CATGAAATTG AACACCTGAG ACAACTTGTT ACAGCTCAAC AGTCACACAT AGACAGCCTG    2580

AAACAGGCGA TGCTGCTTAT CGAATCAAAG CTGCCGACAA CACGGGAGCC AGTGACGCCT    2640

CCCGTGGGGA AAAAATCATG GCAATTCTGG AAGAAATAGC GCTTTCAGCC GGCAAACCGG    2700

CTGAAGCCGG ATCTGCGATT CTGATAACAA ACTAGCAACA CCAGAACAGC CCGTTTGCGG    2760

GCAGCAAAAC CCGTGGGAAT TAATTCCCCT GCTCGCGCAG GCTGGGTGCC AAGCTCTCGG    2820

GTAACATCAA GGCCCGATCC TTGGAGCCCT TGCCCTCCCG CACGATGATC GTGCCGTGAT    2880

CGAAATCCAG ATCCTTGACC CGCAGTTGCA AACCCTCACT GATCCGCATG CCCGTTCCAT    2940

ACAGAAGCTG GGCGAACAAA CGATGCTCGC CTTCCAGAAA ACCGAGGATG CGAACCACTT    3000

CATCCGGGGT CAGCACCACC GGCAAGCGCC GCGACGGCCG AGGTCTTCCG ATCTCCTGAA    3060

GCCAGGGCAG ATCCGTGCAC AGCACCTTGC CGTAGAAGAA CAGCAAGGCC GCCAATGCCT    3120

GACGATGCGT GGAGACCGAA ACCTTGCGCT CGTTCGCCAG CCAGGACAGA AATGCCTCGA    3180

CTTCGCTGCT GCCCAAGGTT GCCGGGTGAC GCACACCGTG GAAACGGATG AAGGCACGAA    3240

CCCAGTGGAC ATAAGCCTGT TCGGTTCGTA AGCTGTAATG CAAGTAGCGT ATGCGCTCAC    3300
```

```
GCAACTGGTC CAGAACCTTG ACCGAACGCA GCGGTGGTAA CGGCGCAGTG GCGGTTTTCA      3360

TGGCTTGTTA TGACTGTTTT TTTGGGGTAC AGTCTATGCC TCGGGCATCC AAGCAGCAAG      3420

CGCGTTACGC CGTGGGTCGA TGTTTGATGT TATGGAGCAG CAACGATGTT ACGCAGCAGG      3480

GCAGTCGCCC TAAAACAAAG TTAAACATCA TGAGGGAAGC GGTGATCGCC GAAGTATCGA      3540

CTCAACTATC AGAGGTAGTT GGCGTCATCG AGCGCCATCT CGAACCGACG TTGCTGGCCG      3600

TACATTTGTA CGGCTCCGCA GTGGATGGCG GCCTGAAGCC ACACAGTGAT ATTGATTTGC      3660

TGGTTACGGT GACCGTAAGG CTTGATGAAA CAACGCGGCG AGCTTTGATC AACGACCTTT      3720

TGGAAACTTC GGCTTCCCCT GGAGAGAGCG AGATTCTCCG CGCTGTAGAA GTCACCATTG      3780

TTGTGCACGA CGACATCATT CCGTGGCGTT ATCCAGCTAA GCGCGAACTG CAATTTGGAG      3840

AATGGCAGCG CAATGACATT CTTGCAGGTA TCTTCGAGCC AGCCACGATC GACATTGATC      3900

TGGCTATCTT GCTGACAAAA GCAAGAGAAC ATAGCGTTGC CTTGGTAGGT CCAGCGGCGG      3960

AGGAACTCTT TGATCCGGTT CCTGAACAGG ATCTATTTGA GGCGCTAAAT GAAACCTTAA      4020

CGCTATGGAA CTCGCCGCCC GACTGGGCTG GCGATGAGCG AAATGTAGTG CTTACGTTGT      4080

CCCGCATTTG GTACAGCGCA GTAACCGGCA AAATCGCGCC GAAGGATGTC GCTGCCGACT      4140

GGGCAATGGA GCGCCTGCCG GCCCAGTATC AGCCCGTCAT ACTTGAAGCT AGACAGGCTT      4200

ATCTTGGACA AGAAGAAGAT CGCTTGGCCT CGCGCGCAGA TCAGTTGGAA GAATTTGTCC      4260

ACTACGTGAA AGGCGAGATC ACCAAGGTAG TCGGCAAATA ATGTCTAACA ATTCGTTCAA      4320

GCCGACGCCG CTTCGCGGCG CGGCTTAACT CAAGCGTTAG ATGCACTAAG CACATAATTG      4380

CTCACAGCCA AACTATCAGG TCAAGTCTGC TTTTATTATT TTTAAGCGTG CATAATAAGC      4440

CCTACACAAA TTGGGAGATA TATCATGAAA GGCTGGCTTT TTCTTGTTAT CGCAATAGTT      4500

GGCGAAGTAA TCGCAACATC CGCATTAAAA TCTAGCGAGG GCTTTACTA               4549
```

(2) INFORMATION FOR SEQ ID NO:25:

(i) SEQUENCE CHARACTERISTICS:
        (A) LENGTH: 199 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

```
GAATTCACTA GTCGATCTGT GCTGTTTGCC ACGGTATGCA GCACCAGCGC GAGATTATGG        60

GCTCGCACGC TCGACTGTCG GACGGGGGCA CTGGAACGAG AAGTCAGGCG AGCCGTCACG       120

CCCTTGACAA TGCCACATCC TGAGCAAATA ATTCAACCAC TAAACAAATC AACCGCGTTT       180

CCCGGAGGTA ACCAAGCTT                                                    199
```

METHOD FOR THE PRODUCTION OF 1,3-PROPANEDIOL BY RECOMBINANT ORGANISMS COMPRISING GENES FOR VITAMIN B12 TRANSPORT

This application claims benefit of Provisional Application No. 60/085,190, filed May 12, 1998.

FIELD OF INVENTION

The present invention relates to the field of molecular biology and the use of recombinant organisms for the production of 1,3-propanediol. More specifically it describes the expression of cloned genes that affect the intracellular transport of vitamin $B_{12}$ in conjunction with genes that effectively convert a carbon substrate to 1,3-propanediol.

BACKGROUND 1,3-Propanediol is a monomer having utility in the production of polyester fibers and the manufacture of polyurethanes and cyclic compounds.

A variety of chemical routes to 1,3-propanediol are known. For example, 1,3-propanediol is prepared 1) from ethylene oxide over a catalyst in the presence of phosphine, water, carbon monoxide, hydrogen and an acid; 2) by the catalytic solution phase hydration of acrolein followed by reduction; or 3) from hydrocarbons such as glycerol, reacted in the presence of carbon monoxide and hydrogen over catalysts having atoms from Group VIII of the periodic table. Although it is possible to generate 1,3-propanediol by these methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups Citrobacter, Clostridium, Enterobacter, Ilyobacter, Klebsiella, Lactobacillus, and Pelobacter. In each case studied, glycerol is converted to 1,3-propanediol in a two-step, enzyme-catalyzed reaction sequence. In the first step, a dehydratase catalyzes the conversion of glycerol to 3-hydroxypropionaldehyde (3-HP) and water (Equation 1). In the second step, 3-HP is reduced to 1,3-propanediol by a $NAD^+$-linked oxidoreductase (Equation 2).

Glycerol→3-HP+$H_2O$ (Equation 1)

3-HP+NADH+$H^+$→1,3-Propanediol+$NAD^+$ (Equation 2)

The 1,3-propanediol is not metabolized further and, as a result, accumulates in high concentration in the media. The overall reaction consumes a reducing equivalent in the form of a cofactor, reduced β-nicotinamide adenine dinucleotide (NADH), which is oxidized to nicotinamide adenine dinucleotide ($NAD^+$).

The production of 1,3-propanediol from glycerol is generally performed under anaerobic conditions using glycerol as the sole carbon source and in the absence of other exogenous reducing equivalent acceptors. Under these conditions, in strains of Citrobacter, Clostridium, and Klebsiella, for example, a parallel pathway for glycerol operates which first involves oxidation of glycerol to dihydroxyacetone (DHA) by a $NAD^+$- (or $NADP^+$-) linked glycerol dehydrogenase (Equation 3). The DHA, following phosphorylation to dihydroxyacetone phosphate (DHAP) by a DHA kinase (Equation 4), becomes available for biosynthesis and for supporting ATP generation via, for example, glycolysis.

Glycerol+$NAD^+$→DHA+NADH+$H^+$ (Equation 3)

DHA+ATP→DHAP+ADP (Equation 4)

In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulons from Citrobacter and Klebsiella have been expressed in *Escherichia coli* and have been shown to convert glycerol to 1,3-propanediol.

The biological production of 1,3-propanediol requires glycerol as a substrate for a two step sequential reaction in which a dehydratase enzyme (typically a coenzyme $B_{12}$-dependent dehydratase) converts glycerol to an intermediate, 3-hydroxypropionaldehyde, which is then reduced to 1,3-propanediol by a NADH-(or NADPH) dependent oxidoreductase. These cofactor requirements are complex and necessitate the use of a whole cell catalyst for an industrial process incorporating this reaction sequence for the production of 1,3-propanediol. A process for the production of 1,3-propanediol from glycerol using an organism containing a coenzyme $B_{12}$-dependent diol dehydratase is described in U.S. Pat. No. 5,633,362 (Nagarajan et al.). However, the process is not limited to the use of glycerol as feedstock. Glucose and other carbohydrates are suitable substrates and, recently, these substrates have been shown to be substrates for 1,3-propanediol production. Carbohydrates are converted to 1,3-propanediol using mixed microbial cultures where the carbohydrate is first fermented to glycerol by one microbial species and then converted to 1,3-propanediol by a second microbial species. U.S. Pat. No. 5,599,689 (Haynie et al.). For reasons of simplicity and economy, a single organism able to convert carbohydrates to 1,3-propanediol is preferred. Such an organism is described in U.S. Pat. No. 5,686,279 (Laffend et al.).

Some bacteria, such as Salmonella or Klebsiella, are able to synthesize coenzyme $B_{12}$ to enable a diol or glycerol dehydratase to operate, but other species must transport $B_{12}$ from outside of the cell. The term "$B_{12}$" is used to refer collectively to coenzyme $B_{12}$; derivatives of coenzyme $B_{12}$ where the upper axial 5'-deoxyadenosyl ligand is replaced with another ligand (for example, an aquo-, cyano- or methyl group); and the radical species, cob(II)alamin.

$B_{12}$ transport into bacteria presents two major problems. First, the $B_{12}$ molecule is too large for passage through outer membrane porins, thus requiring a specific outer membrane transport system. Second, owing to the scarcity of $B_{12}$ in the environment, the outer membrane transport system must have a high affinity for $B_{12}$ and move it into the periplasm for subsequent transport by another system across the inner membrane. For *E. coli*, which is unable to synthesize the corrin ring of $B_{12}$, an external supply of $B_{12}$ is required for growth under certain conditions. These requirements may be modest; when a functional 5-methyltetrahydrofolate-homocysteine methyltransferase (MetH) is present ~25 $B_{12}$ molecules (methylcobalamin) are required and ~500 coenzyme $B_{12}$ molecules are needed for ethanolamine ammonia-lyase dependent growth.

Several proteins are required for the transport process. The 66 kDa outer membrane protein BtuB serves as the high affinity ($K_d$=0.3 nM) receptor for adenosyl-, aquo-, cyano- and methyl cobalamins and the corresponding cobinamides. When grown in the absence of $B_{12}$ or at low levels (<1 nM) ~200 copies of BtuB are present per cell. However, the growth of cells in media containing high levels of $B_{12}$ (>0.1 uM) represses synthesis of BtuB, and even at levels of 5 nM uptake activities are repressed 80–90%. Unlike Salmonella, the *E. coli* BtuB is not repressed by aerobiosis. Transport into the periplasm requires the interaction of BtuB with a 26 kDa inner membrane protein TonB in an energy-dependent process that also requires co-transport of calcium. In fact, the high affinity binding of $B_{12}$ to BtuB is calcium dependent and there is evidence for a reciprocal $B_{12}$ dependent calcium binding site with a $K_d$ for calcium of ~30 nM at pH 6.6 at saturating levels of $B_{12}$. This affinity for calcium decreases with decreasing pH. TonB uses proton motive force to drive a structural alteration needed for transport. In the absence of TonB, $B_{12}$ penetrates die outer membrane with very low efficiency. TonB also energizes outer-membrane transport systems for iron, including the FepA and FhuA systems. Thus BtuB competes with these systems for TonB activity. In the absence of protein synthesis, the rate of $B_{12}$ transport decreases with a half life of ~20 min and is attributable to a loss of TonB activity. Transfer of $B_{12}$ from BtuB to the periplasmic binding protein is poorly characterized and may involve a protein encoded by the btuF locus, at least in Salmonella.

Transport across the inner membrane is mediated by the BtuC and BtuD proteins encoded by the btuCED operon. BtuC and BtuD resemble transport proteins requiring a periplasmic binding protein, and BtuD has an ATP binding site. Mutant phenotypes of these two genes are corrected by a modest increase in external $B_{12}$, and it is thought that the BtuB/TonB system concentrates $B_{12}$ in the periplasm and fortuitous transport of $B_{12}$ is thus facilitated into the cytoplasm. BtuE may not be involved in transport and its function is unknown. The btuCED operon appears to be expressed constitutively and is not regulated by the presence of $B_{12}$ in the growth medium.

The transport pathway can be summarized as an initial binding of $B_{12}$ to the outer membrane protein BtuB, followed by interaction with the inner membrane protein TonB and the energy-dependent translocation and binding to periplasmic BtuF, and finally transfer to die inner membrane proteins BtuCD and translocation to the cytoplasm.

An important control mechanism for $B_{12}$ transport is the influence of coenzyme $B_{12}$ on the levels of the outer membrane protein BtuB. The formation of cellular coenzyme $B_{12}$ results from the activity of ATP:corrinoid adenosyltransferase, encoded by the btuR gene. As noted above, the presence of $B_{12}$ in media results in a reduction in BtuB function, but it is important to emphasize that this direct repression is observed only with coenzyme $B_{12}$ and not with coenzyme $B_{12}$ precursors, as seen by the addition of various $B_{12}$ molecules to a btuR-defective strain. Coenzyme $B_{12}$ precursors supplied in the media may cause repression resulting from its conversion into coenzyme $B_{12}$. Control appears to alter continuation of message synthesis rather than initiation, so the use of foreign promoters for btuB expression does not necessarily afford protection from regulation by coenzyme $B_{12}$. An unusual feature of btuB regulation is that repression seems to be as effective when the btuB gene is carried on a multicopy plasmid as when in a single copy. This apparent lack of titration by excess copies of the target sequences suggests a large excess of the repressor (coenzyme $B_{12}$) in the cell.

By gene fusion studies it appears that both transcriptional and translational control applies to btuB expression and, considered together, these various features suggest a mechanism in which a direct interaction occurs between coenzyme $B_{12}$ and the mRNA leader. This interaction may induce mRNA folding to stabilize the hairpin thereby blocking ribosome access to the translational start. The requirement for a substantial portion of the btuB transcript in control of its own expression and regulation suggests that post-transcriptional events involving the leader and btuB coding region influence both transcriptional read through and translation initiation. Involvement of transcribed regions in regulation has been documented for attenuation control in amino acid biosynthetic pathways, but the unusual features of btuB regulation are that important regulatory sites are located within the btuB coding sequence and that this regulation affects both transcription and translation.

The problem to be solved by the present invention is how to biologically produce 1,3-propanediol by means of a single recombinant organism containing a coenzyme $B_{12}$-dependent dehydratase enzyme enhancing the availability of coenzyme $B_{12}$ to the enzyme by the presence of foreign genes encoding activities responsible for $B_{12}$ transport.

SUMMARY OF THE INVENTION

Applicants have solved the stated problem by providing a single recombinant organism capable of the dehydratase-mediated bioconversion of a fermentable carbon source directly to 1,3-propanediol, where coenzyme $B_{12}$ availability to the enzyme is enhanced by the presence of $B_{12}$ transport genes. Preferred substrates are glucose and glycerol from a larger set of substrates including fermentable carbohydrates, single carbon substrates and mixtures thereof.

The present invention provides a process for the bioproduction of 1,3-propanediol comprising: (i) contacting a transformed host cell with at least one fermentable carbon source and an effective amount of vitamin $B_{12}$ whereby 1,3-propanediol is produced, the transformed host cell comprising: (a) at least one copy of a gene encoding a protein having a dehydratase activity; (b) at least one copy of a gene encoding a protein having an oxidoreductase activity; (c) at least one copy of a gene encoding a vitamin $B_{12}$ receptor precursor protein; (d) at least one copy of a gene encoding a vitamin $B_{12}$ transport system permease protein; and (e) at least one copy of a gene encoding vitamin $B_{12}$ transport ATP- or GTP-binding protein; wherein at least one of the genes of (c), (d) or (e) is introduced into the host cell, and (ii) recovering the 1,3-propanediol produced from step (i). The effective amount of vitamin $B_{12}$ is at a 0.1 to 10.0 fold molar ratio to the amount of dehydratase present.

The invention further provides a transformed host cell expressing a dehydratase enzyme containing (a) at least one copy of a gene encoding a protein having a dehydratase activity; (b) at least one copy of a gene having an oxidoreductase activity; (c) at least one copy of a gene encoding a vitamin $B_{12}$ receptor precursor (BtuB); (d) at least one copy of a gene encoding a vitamin $B_{12}$ transport system permease protein (BtuC); and (e) at least one copy of a gene encoding vitamin $B_{12}$ transport ATP-binding protein (BtuD), wherein at least one copy of the gene of (c), (d), or (e) is introduced into die host cell.

BRIEF DESCRIPTION OF SEQUENCE LISTING

Applicants have provided 25 sequences in conformity with Rules for the Standard Representation of Nucleotide and Amino Acid Sequences in Patent Applications (Annexes I and II to the Decision of the President of the EPO, published in Supplement No. 2 to OJ EPO, 12/1992), with 37 C.F.R. 1.821–1.825 and Appendices A and B (Requirements for Application Disclosures Containing Nucleotides and/or Amino Acid Sequences) with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO:1 is the nucleotide sequence for an *E. coli* btuB, encoding the vitamin $B_{12}$ receptor precursor protein.

SEQ ID NO:2 is the nucleotide sequence for a Salmonella btuB, encoding the vitamin $B_{12}$ receptor precursor protein.

SEQ ID NO:3 is the nucleotide sequence for a *E. coli* btuC, encoding the vitamin $B_{12}$ transport system permease protein.

SEQ ID NO:4 is the nucleotide sequence for a *E. coli* btuD, encoding the vitamin $B_{12}$ transport ATP-binding protein.

SEQ ID NO:5 is the nucleotide sequence for a *E. coli* btuE, encoding the vitamin $B_{12}$ transport periplasmic protein.

SEQ ID NO:6 is the nucleotide sequence for dhaB1, encoding the α subunit of the glycerol dehydratase enzyme.

SEQ ID NO:7 is the nucleotide sequence for dhaB2, encoding the β subunit of the glycerol dehydratase enzyme.

SEQ ID NO:8 is the nucleotide sequence for dhaB3, encoding the γ subunit of the glycerol dehydratase enzyme.

SEQ ID NO:9 is the nucleotide sequence for dhaT, encoding Klebsiella oxidoreductase enzyme.

SEQ ID NO:10 is the nucleotide sequence for PHK28-26 a 12.1 kb EcoRI-SalI fragment containing the dha operon.

SEQ ID NO:11 is the nucleotide sequence for a multiple cloning site and terminator sequence used in the construction of the expression vector pTacIQ.

SEQ ID NO:12–23 are primers used in the construction of expression vectors of the present invention.

SEQ ID NO:24 is the nucleotide sequence for an insert in pCL1920, used in the construction of the expression cassette for dhaT and dhaB(1,2,3).

SEQ ID NO:25 is the nucleotide sequence for the glucose isomerase promoter sequence from Streptomyces.

DETAILED DESCRIPTION OF THE INVENTION

The present invention provides a method for biologically producing 1,3-propanediol from a fermentable carbon source in a single recombinant organism. The method incorporates a microorganism containing genes encoding glycerol dehydratase, 1,3-propanediol oxidoreductase, a gene encoding vitamin $B_{12}$ receptor precursor(BtuB), a gene encoding vitamin $B_{12}$ transport system permease protein (BtuC), and a gene encoding vitamin $B_{12}$ transport ATP-binding protein (BtuD). The recombinant microorganism is contacted with a carbon substrate and 1,3-propanediol is isolated from the growth media.

The present method provides a rapid, inexpensive and environmentally responsible source of 1,3-propanediol monomer useful in the production of polyesters and other polymers.

The following definitions are to be used to interpret the claims and specification.

The terms "vitamin $B_{12}$ receptor precursor", "BtuB" or "outer membrane vitamin $B_{12}$ receptor protein" refer to the polypeptide located on the outer membrane of bacteria responsible for the transport of coenzyme $B_{12}$, cyanocobalamin, aquacobalamin, methycobalamin, and cobinamide from the culture media to the periplasmic space. For the purposes of the present invention BtuB includes, for example, the proteins encoded by the btuB genes of *Escherichia coil* (GenBank M10112) (SEQ ID NO:1), and of *Salmonella typhimurium (GenBank M*89481) (SEQ ID NO:2).

The terms "BtuC" or "vitamin $B_{12}$ transport system permease protein" refer to the polypeptide located on the inner membrane of bacteria, that together with BtuD, transports vitamin $B_{12}$ and coenzyme $B_{12}$ from the periplasmic space to the cytoplasm. BtuC includes, for example, the polypeptide encoded by the btuC gene of *E. coil* (GenBank M14031) (SEQ ID NO:3).

The terms "BtuD" or "vitamin $B_{12}$ transport ATP-binding protein" refer to the polypeptide located on the inner membrane of bacteria, that together with BtuC, transports vitamin $B_{12}$ or coenzyme $B_{12}$ from the periplasmic space to the cytoplasm. BtuD includes, for example, the polypeptide encoded by the btuD gene of *E. coil* (GenBank M 14031) (SEQ ID NO:4).

The term "BtuE" refers to the polypeptide encoded by the btuE gene of *E. coli* (GenBank M14031) (SEQ ID NO:5) and is an auxiliary component of the transport system.

The terms "glycerol dehydratase" or "dehydratase enzyme" refer to the polypeptide(s) responsible for a coenzyme $B_{12}$-dependent enzyme activity that is capable of isomerizing or converting a glycerol molecule to the product 3-hydroxypropionaldehyde. For the purposes of the present invention, the dehydratase enzymes include a glycerol dehydratase (GenBank U09771, U30903) and a diol dehydratase (GenBank D45071) having preferred substrates of glycerol and 1,2-propanediol, respectively. Glycerol dehydratase of *K. pneumoniae* ATCC 25955 is encoded by the genes dhaB1, dhaB2, and dhaB3 identified as SEQ ID NOS:6, 7, and 8 respectively. The dhaB1, dhaB2 and dhaB3 genes code for the α, β, and γ subunits of the glycerol dehydratase enzyme, respectively. Glycerol dehydratase and diol dehydratase enzymes are complexes (with an $α_2β_2γ_2$ subunit composition) that bind coenzyme $B_{12}$ with a 1:1 stoichiometry.

An "effective amount" of coenzyme $B_{12}$ precursor (or vitamin $B_{12}$) will mean that coenzyme $B_{12}$ precursor (or vitamin $B_{12}$) is present in the system at a molar ratio of between 0.1 and 10, relative to the dehydratase enzyme.

The terms "oxidoreductase" or "1,3-propanediol oxidoreductase" refer to the polypeptide(s) responsible for an enzyme activity that is capable of catalyzing the reduction of 3-hydroxypropionaldehyde to 1,3-propanediol. 1,3-Propanediol oxidoreductase includes, for example, the polypeptide encoded by the dhaT gene (GenBank U09771, U30903) and is identified as SEQ ID NO:9.

The terms "coenzyme $B_{12}$" and "adenosylcobalamin" are used interchangeably to mean 5'-deoxyadenosylcobalamin. Hydroxocobalamin is the derivative of coenzyme $B_{12}$ where the upper axial 5'-deoxyadenosyl ligand is replaced with a hydroxy moiety. Aquacobalamin is the protonated form of hydroxocobalamin. Methylcobalamin is the derivative of coenzyme $B_{12}$ where the upper axial 5'-deoxyadenosyl ligand is replaced with a methyl moiety. The term "cyanocobalamin" is used to refer to the derivative of coenzyme $B_{12}$ where the upper axial 5'-deoxy'5'-adenosyl ligand is replaced with a cyano moiety. The terms "vitamin $B_{12}$" and "$B_{12}$" are used interchangeably to refer collectively to coenzyme $B_{12}$, derivatives of coenzyme $B_{12}$ where the upper axial 5'-deoxyadenosyl ligand is replaced with another ligand, for example, an aquo-, cyano- or methyl group; and the radical species, cob(II)alamin. The term "coenzyme $B_{12}$ precursor" refers to a derivation of coenzyme $B_{12}$ where the upper axial 5'-deoxyadenosyl ligand is replaced. An "effective amount" of coenzyme $B_{12}$ precursor will mean that coenzyme $B_{12}$ precursor is present in the system at approximately a 0.1- to 10.0-fold molar ratio to the amount of dehydratase enzyme present.

The terms "polypeptide" and "protein" are used interchangeably.

The terms "fermentable carbon substrate" and "fermentable carbon source" refer to a carbon source capable of being metabolized by host organisms of the present invention and particularly carbon sources selected from the group consisting of monosaccharides, oligosaccharides, polysaccharides, glycerol, dihydroxyacetone and one-carbon substrates or mixtures thereof The terms "host cell" or "host organism" refer to a microorganism capable of receiving foreign or heterologous genes or multiple copies of endogenous genes and of expressing those genes to produce an active gene product.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "encoding" and "coding" refer to the process by which a gene, through the mechanisms of transcription and translation, produces an amino acid sequence. The process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue (such as glycine), or a more hydrophobic residue (such as valine, leucine, or isoleucine). Similarly, changes which result in substitution of one negatively charged residue for another (such as aspartic acid for glutamic acid), or one positively charged residue for another (such as lysine for arginine), can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in its host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The term "genetically altered" refers to the process of changing hereditary material by transformation or mutation.

The present invention involves the construction of a production organism that incorporates the genetic machinery necessary to convert a fermentable carbon substrate to 1,3-propanediol, in conjunction with genes encoding enzymes needed for the intracellular transport of vitamin $B_{12}$. The genes involved in 1,3-propanediol production will include a dehydratase gene (typically a glycerol or diol dehydratase) and an oxidoreductase as well as other proteins expected to aid in the assembly or in maintaining the stability of the dehydratase enzyme. These genes may transgenes and introduced into the host cell, or may be endogenous. Genes responsible for the intracellular transport of vitamin $B_{12}$ will include at least one gene encoding a vitamin $B_{12}$ receptor precursor protein(BtuB), at least one gene encoding a gene encoding vitamin $B_{12}$ transport system permease protein(BtuC) and at least one gene encoding vitamin $B_{12}$ transport ATP-binding protein (BtuD). At least one of these genes will be a transgene and introduced into the production cell. The transformed production cell is then grown under appropriate conditions for the production of 1,3-propanediol.

Recombinant organisms containing the necessary genes that will encode the enzymatic pathway for the conversion of a carbon substrate to 1,3-propanediol may be constructed using techniques well known in the art. In the present invention genes encoding glycerol dehydratase (dhaB) and 1.3-propanediol oxidoreductase (dhaT) were isolated from a native host such as Klebsiella, and together with genes encoding BtuB (btuB), BtuC (btuC), BtuD (btuD), and BtuE (btuE) isolated from native hosts such as *E. coli* and *S. typhimurium* are used to transform host strains such as *E. coli* strain DH5α or FM5; *K. pneumoniae* strain ATCC 25955; *K. oxytoca* strain ATCC 8724 or M5al, *S. cerevisiae* strain YPH499, *P. pastoris* strain GTS115, or *A. niger* strain FS1.

Rationale for dhaB, dhaT

The production of 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases which are known to be non-specific with respect to their substrates or the activity can be introduced into the host by recombination. The reduction step can be catalyzed by a NAD$^+$(or NADP$^+$) linked host enzyme or the activity can be introduced into the host by recombination. It is notable that the dha regulon contains a glycerol dehydrogenase (E.C. 1.1.1.6) which catalyzes the reversible reaction of Equation 3.

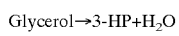
Glycerol→3-HP+H$_2$O (Equation 1)

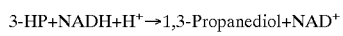
3-HP+NADH+H$^+$→1,3-Propanediol+NAD$^+$ (Equation 2)

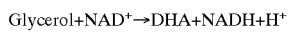
Glycerol+NAD$^+$→DHA+NADH+H$^+$ (Equation 3)

Glycerol is converted to 1,3-propanediol via the intermediate 3-hydroxy-propionaldehye (3-HP) as has been described in detail above. The intermediate 3-HP is produced from glycerol, Equation 1, by a dehydratase enzyme which can be encoded by the host or can introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HP, Equation 2, by a NAD$^+$- (or NADP$^+$) linked host enzyme or the activity can introduced into tie host by recombination. This final reaction in the production of 1,3-propanediol can be catalyzed by 1,3-propanediol dehydrogenase (E.C. 1.1.1.202) or other alcohol dehydrogenases.

The dha regulon is comprised of several functional elements including dhaK encoding dihydroxyacetone kinase, dhaD encoding glycerol dehydrogenase, dhaR encoding a regulatory protein, dhaT encoding 1,3-propanediol oxidoreductase as well as dhaB1, dhaB2, and dhaB3 encoding the α, β and γ subunits of the enzyme, respectively. Additionally, gene products designated as protein X, protein 1, protein 2, and protein 3 (corresponding to dhaBX, orfY, orfX, and orfW, respectively) are encoded within the dha regulon. While the precise functions of these gene products are not well characterized, the genes are linked to glycerol dehydratase (dhaB) or 1,3-propanediol oxidoreductase (dhaT) and are known to be useful for the production of 1,3-propanediol. Coenzyme $B_{12}$ that is bound to glycerol dehydratase occasionally undergoes irreversible cleavage to form an inactive modified coenzyme which is tightly bound to the dehydratase. Reactivation of the enzyme occurs by exchange of the bound, modified coenzyme with free, intact coenzyme $B_{12}$. Protein X and at least one other of protein 1, protein 2, and protein 3 are involved in the exchange process. (See U.S. Ser. No. 08/969,683). In the separate diol dehydratase system, genes designated as ddrA and ddrB, corresponding to the genes encoding protein X and protein 2, respectively, are described to be involved in the exchange process. Mori et al., *J. Biol Chem.* 272, 32034–32041 (1997).

It is contemplated that glycerol-3-phosphate dehydrogenase and glycerol-3-phosphatase may be particularly effective in the conversion of glucose to glycerol, required for the production of 1,3-propanediol. The term "glycerol-3-phosphate dehydrogenase" refers to a polypeptide responsible for an enzyme activity that catalyzes the conversion of dihydroxyacetone phosphate (DHAP) to glycerol-3-phosphate (G3P). In vivo G3PDH may be NADH, NADPH, or FAD-dependent. The NADH-dependent enzyme (EC 1.1.1.8) is encoded, for example, by several genes including GPD1 (GenBank Z74071×2), or GPD2 (GenBank Z35169×1), or GPD3 (GenBank G984182), or DAR1 (GenBank Z74071×2). The NADPH-dependent enzyme (EC 1.1.1.94) is encoded by gpsA (GenBank U321643, (cds 197911-196892) G466746 and L45246). The FAD-dependent enzyme (EC 1.1.99.5) is encoded by GUT2 (GenBank Z47047×23), or glpD (GenBank G147838), or glpABC (GenBank M20938). The term "glycerol-3-phosphatase" refers to a polypeptide responsible for an enzyme activity that catalyzes the conversion of glycerol-3-phosphate and water to glycerol and inorganic phosphate. Glycerol-3-phosphatase is encoded, for example, by GPP1 (GenBank Z47047×125), or GPP2 (GenBank U18813×11).

Gene Isolation

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, cosmid libraries may be created where large segments of genomic DNA (35–45 kb) may be packaged into vectors and used to transform appropriate hosts. Cosmid vectors are unique in being able to accommodate large quantities of DNA. Generally, cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook et al., *Molecular Cloning: A Laboratory Manual*, Second Edition (1989) Cold Spring Harbor Laboratory Press, Cold Spring Harbor, N.Y. (1989).

Typically to clone cosmids, foreign DNA is isolated and ligated, using the appropriate restriction endonucleases, adjacent to the cos region of the cosmid vector. Cosmid vectors containing the linearized foreign DNA are then reacted with a DNA packaging vehicle such as bacteriophage λ. During the packaging process the cos sites are cleaved and the foreign DNA is packaged into the head portion of the bacterial viral particle. These particles are then used to transfect suitable host cells such as *E. coli*. Once injected into die cell, the foreign DNA circularizes under the influence of the cos sticky ends. In this manner large segments of foreign DNA can be introduced and expressed in recombinant host cells.

Isolation and Cloning of Genes Encoding Glycerol Dehydratase (dhaB) and 1.3-propanediol Oxidoreductase (dhaT)

Methods for the identification and isolation of dhaB and dhaT were done essentially as described in U.S. Pat. No. 5,686,276 and hereby incorporated by reference. Cosmid vectors and cosmid transformation methods were used within tie context of the present invention to clone large segments of genomic DNA from bacterial genera known to possess genes capable of processing glycerol to 1,3-propanediol. Two 1,3-propanediol positive transformants were analyzed and DNA sequencing revealed extensive homology to the glycerol dehydratase gene (dhaB) from *C. freundii*, demonstrating that these transformants contained DNA encoding the glycerol dehydratase gene. dhaB and dhaT were isolated and cloned into appropriate expression cassettes for co-expression in recombinant hosts with genes encoding $B_{12}$ transport functions.

Although the instant invention utilizes the isolated genes from within a Klebsiella cosmid, alternate sources of dehydratase genes include, but are not limited to, Citrobacter, Clostridia, and Salmonella.

$B_{12}$ Transport Genes

D Rationale for $B_{12}$ Transport Genes

Adenosyl-cobalamin (coenzyme $B_{12}$) is an essential cofactor for glycerol dehydratase activity. The coenzyme is the most complex non-polymeric natural product known, and its synthesis in vivo is directed using the products of about 30 genes. Synthesis of coenzyme $B_{12}$ is found in prokaryotes, some of which are able to synthesize the compound de novo, while others can perform partial reactions. *E. coli*, for example, cannot fabricate the corrin ring structure, but is able to catalyze the conversion of cobinamide to corrinoid and can introduce the 5'-deoxyadenosyl group.

$B_{12}$ transport into *E. coli* may be a limiting factor for the production of a functional DhaB enzyme, in which case increased intracellular availability of coenzyme $B_{12}$ would be required to optimize glycerol dehydratase activity (and, ultimately, 1,3-propanediol production). This may be achieved by increasing the rate of transport of $B_{12}$ into the cell. Given the role of coenzyme $B_{12}$ as a repressor of btuB expression, and the levels of coenzyme $B_{12}$ required in fermentations, it is likely that $B_{12}$ transport declines over time due to turnover or dilution of BtuB from cell division. The available pool of free coenzyme $B_{12}$ in the cell will be influenced by the rate of uptake, the relative affinities of BtuB mRNA and DhaB for coenzyme $B_{12}$, and the concentrations of the mRNA and DhaB. Since uptake is reduced when using $B_{12}$ enriched media, an important factor determining whether the uptake mechanism is restored will be partitioning of coenzyme $B_{12}$ between its regulatory role on btuB expression and DhaB enzyme. This presents an unusual problem of a desired cofactor (coenzyme $B_{12}$) being responsible for its own limitation. The use of media containing coenzyme $B_{12}$ precursors in place of coenzyme $B_{12}$ may alleviate the problem, but this will only be a temporary gain since the transported precursors will be converted to coenzyme $B_{12}$ by the btuR-encoded adenosyltransferase. One way to circumvent this gene regulation problem is to uncouple BtuB synthesis from coenzyme $B_{12}$ regulation. Amplification of btuB expression by cloning on multicopy plasmids leads to increased binding of $B_{12}$ to membranes and increased rates of uptake, and if the btuB native promoter is replaced, will also uncouple synthesis of BtuB from coenzyme $B_{12}$ regulation.

$B_{12}$ transport into bacteria requires a specific transport system. Several proteins are required for this transport process. The 66 kDa outer membrane protein BtuB serves as a receptor for adenosyl-, aquo-, cyano- and methyl cobalamins and the corresponding cobinamides. Transport into the periplasm requires the interaction of BtuB with a 26 kDa inner membrane protein TonB in an energy-dependent process. Transport across the inner membrane is mediated by the BtuC and BtuD proteins encoded by the btuCED operon. BtuC and BtuD resemble transport proteins requiring a periplasmic binding protein, and BtuD has an ATP binding site. The transport pathway can be summarized as an initial binding of $B_{12}$ to the outer membrane protein BtuB, followed by interaction with the inner membrane protein TonB and the energy-dependent translocation and binding to periplasmic BtuF (in *S. typhimurium*), and finally transfer to the inner membrane proteins BtuCD and translocation to the cytoplasm. Amplification of btuBCED expression by cloning on multicopy plasmids leads to increased binding of $B_{12}$ to membranes and increased rates of uptake into cells.

Isolation and Expression of the $B_{12}$ Transport Genes

Expression plasmids that could exist as replicating elements in *E. coli* were constructed for the four $B_{12}$ transport genes, btuB, btuC, btuD and btuE. The four genes were isolated by PCR using gene-specific primers and *E. coli* chromosomal DNA. The four genes were assembled together on expression plasmids. All expression plasmids use a trc promoter for transcription and the native btu ribosome binding sites for translation. Each plasmid also contained either 1) a gene for β-lactamase for selection in *E. coli* on media containing ampicillin or 2) a gene encoding chloramphenicol acetytransferase for selection on media containing chloramphenicol. Plasmid origins of replication are either ColE1 or p15A.

Host Cells

Suitable host cells for the recombinant production 1,3-propanediol by the coexpression of a gene encoding a dehydratase enzyme and the genes responsible for intracellular $B_{12}$ transport may be either prokaryotic or eukaryotic and will be limited only by their ability to express active enzymes. Preferred hosts will be those typically useful for production of 1,3-propanediol or glycerol such as Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces and Pseudomonas. Most preferred in the present invention are *E. coli*, Klebsiella species, and Saccharomyces species.

*E. coli*, Saccharomyces species, and Klebsiella species are particularly preferred hosts. Strains of *Klebsiella pneumoniae* are known to produce 1,3-propanediol when grown on glycerol as the sole carbon. It is contemplated that Klebsiella can be genetically altered to produce 1,3-propanediol from monosaccharides, oligosaccharides, polysaccharides, or one-carbon substrates.

Vectors and Expression Cassettes

The present invention provides a variety of vectors and transformation and expression cassettes suitable for the cloning, transformation and expression of genes encoding a suitable dehydratase and genes effecting the intracellular transport of $B_{12}$ to into a suitable host cell. Suitable vectors will be those which are compatible with the bacterium employed. Suitable vectors can be derived, for example, from a bacteria, a virus (such as bacteriophage T7 or a M-13 derived phage), a cosmid, a yeast, or a plant. Protocols for obtaining and using such vectors are known to those in the art. (Sambrook et al., Molecular Cloning: A Laboratory Manual—volumes 1,2,3 (Cold Spring Harbor Laboratory, Cold Spring Harbor, N.Y., (1989)).

Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell although it is to be understood that such control regions need not be derived from the genes native to the specific species chosen as a production host.

Initiation control regions or promoters, which are useful to drive expression of the relevant genes of the present invention in the desired host cell, are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Transformation of Suitable Hosts and Expression of Genes for the Production of 1.3-propanediol Once suitable cassettes are constructed they are used to transform appropriate host cells. Introduction into the host cell of the cassette containing the genes responsible for intracellular $B_{12}$ transport as well as glycerol dehydratase (dhaB), and 1,3-propanediol oxidoreductase (dhaT), either separately or together, may be accomplished by known procedures such as by transformation (e.g., using calcium-permeabilized cells, electroporation) or by transfection using a recombinant phage virus. (Sambrook et al., supra.)

In the present invention, *E. coli* FM5 containing the genes encoding glycerol dehydratase (dhaB), 1,3-propanediol oxidoreductase (dhaT), BtuB (btuB), BtuC (btuC), BtuD (btuD), and BtuE (btuE) is used to transport vitamin $B_{12}$ or coenzyme $B_{12}$ from the media into the cytoplasm to enable glycerol dehydratase to function.

Media and Carbon Substrates

Fermentation media in the present invention must contain suitable carbon substrates. Suitable substrates may include but are not limited to glycerol, dihydroxyacetone, monosaccharides such as glucose and fructose, oligosaccharides such as lactose or sucrose, polysaccharides such as starch or cellulose, or mixtures thereof, and unpurified mixtures from renewable feedstocks such as cheese whey permeate, corn-steep liquor, sugar beet molasses, and barley malt. Additionally, the carbon substrate may also be one-carbon substrates (such as carbon dioxide or methanol) for which metabolic conversion into key biochemical intermediates has been demonstrated.

Glycerol production from single carbon sources (e.g., methanol, formaldehyde, or formate) has been reported in methylotrophic yeasts (Yamada et al., *Agric. Biol. Chem.*, 53(2) 541–543, (1989)) and in bacteria (Hunter et al., *Biochemistry*, 24, 4148–4155, (1985)). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, *Bacterial Metabolism,* Second Edition, Springer-Verlag: New York (1986)). The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to utilization of one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd*, [Int. Symp.], 7th (1993), 415–32. Editor(s): Murrell, J. Collin; Kelly, Don P. Publisher: Intercept, Andover, UK). Similarly, various species of Candida will metabolize alanine or oleic acid (Sulter et al., *Arch. Microbiol.,* 153(5), 485–9 (1990)). Accordingly, the source of carbon utilized in the present invention may encompass a wide variety of carbon-containing substrates and will only be limited by the requirements of the host organism.

Although it is contemplated that all of the above-mentioned carbon substrates and mixtures thereof are suitable in the present invention, preferred carbon substrates are glycerol, dihydroxyacetone, monosaccharides, oligosaccharides, polysaccharides, and one-carbon substrates. More preferred are sugars such as glucose, fructose, sucrose and single carbon substrates such as methanol and carbon dioxide. Most preferred is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production. Particular attention is given to Co(II) salts and coenzyme $B_{12}$ precursors. For example, *E. coli* and eukaryotes are unable to synthesize coenzyme $B_{12}$ de novo but are able to utilize coenzyme $B_{12}$ precursors. Preferred coenzyme $B_{12}$ precursors are cyanocobalamin and hydroxocobalamin. It is desirable that the amount of coenzyme $B_{12}$ inside the host cell be approximately equal in molar concentration to the amount of dehydratase enzyme.

Culture Conditions

Typically, cells are grown at 30° C. in appropriate media. Preferred growth media in the present invention are common commercially prepared media such as Luria Bertani (LB) broth, Sabouraud Dextrose (SD) broth or Yeast Malt Extract (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 3':5'-monophosphate, may also be incorporated into the reaction media. Similarly, the use of agents known to modulate enzymatic activities (e.g., sulphites, bisulphites and alkalis) that lead to enhancement of glycerol production may be used in conjunction with or as an alternative to genetic manipulations.

Suitable pH ranges for the fermentation are between pH 5.0 to pH 9.0, where pH 6.0 to pH 8.0 is preferred as the range for the initial condition.

Reactions may be performed under aerobic or anaerobic conditions where anaerobic or microaerobic conditions are preferred.

Fermentations

The present invention may be practiced using either batch, Fed-Batch, or continuous processes and that any known mode of fermentation would be suitable. Additionally, it is contemplated that cells may be immobilized on a substrate as whole cell catalysts and subjected to fermentation conditions for 1,3-propanediol production.

The present process is exemplified herein as a batch method of fermentation. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a batch fermentation is "batch" with respect to the addition of the carbon source and attempts are often made at controlling factors such as pH and oxygen concentration. The metabolite and biomass compositions of the batch system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch fermentation system which is also suitable in the present invention. In this variation of a typical batch system, the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and die partial pressure of waste gases such as $CO_2$. Batch and Fed-Batch fermentations are common and well known in the art and examples may be found in Brock, infra.

The method would also be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology. A variety of methods are detailed by Brock, infra.

Identification and Purification of 1,3-propanediol

Methods for the purification of 1,3-propanediol from fermentation media are known in the art. For example, propanediols can be obtained from cell media by subjecting the reaction mixture to extraction with an organic solvent, distillation, and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media are analyzed on an analytical ion exchange column using a mobile phase of 0.01 N sulfuric acid in an isocratic fashion.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures for phosphorylations, ligations, and transformations are well known in the art. Techniques suitable for use in the following examples may be found in Sambrook, J. et al., *Molecular Cloning: A Laboratory Manual*, Second Edition, Cold Spring Harbor Laboratory Press, Cold Spring Harbor, N.Y. (1989).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Isolation and Identification 1,3-propanediol

The conversion of glycerol to 1,3-propanediol was monitored by HPLC. Analyses were performed using standard techniques and materials available to one skilled in the art of chromatography. One suitable method utilized a Waters Maxima 820 HPLC system using UV (210 nm) and RI detection. Samples were injected onto a Shodex SH-1011 column (8×300 mm, purchased from Waters, Milford, Mass.) equipped with a Shodex SH-1011P precolumn (6 mm×50 mm), temperature controlled at 50° C., using 0.01 N $H_2SO_4$ as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated were compared to that of authentic 1,3-propanediol (m/e: 57, 58).

An alternative method for GC/MS involved derivatization of the sample. To 1.0 mL of sample (e.g., culture supernatant) was added 30 uL of concentrated (70% v/v) perchloric acid. After mixing, the sample was frozen and lyophilized. A 1:1 mixture of bis(trimethylsilyl)trifluoroacetamide:pyridine (300 uL) was added to the lyophilized material, mixed vigorously and placed at 65° C. for one h. The sample was clarified of insoluble material by centrifugation. The resulting liquid was partitioned into two phases, the upper of which was used for analysis. The sample was chromatographed on a DB-5 column (48 m, 0.25 mm I.D., 0.25 um film thickness; from J&W Scientific) and the retention time and mass spectrum of the 1,3-propanediol derivative obtained from culture supernatants were compared to that obtained from authentic standards. The mass spectrum of TMS-derivatized 1,3-propanediol contains the characteristic ions of 205, 177, 130 and 115 AMU.

Identification of Vitamin or Coenzyme $B_{12}$

Cell free samples were run on HPLC for coenzyme $B_{12}$ and cyanocobalamin (cyanocobalamin) quantification. Cobalamin quantification was achieved via first comparing peak area ratios at 278 nm and 361 nm with standards, and then applying peak areas to standard curves of the cobalamins.

HPLC Method

Column:
 Supelcosil LC-18-DB, 25 cm×4.6 mm (Supelco, Inc., Bellefonte, Pa.)
 Supelcosil LC-18-DB Precolumn kit
Column Temp: Ambient
Sample Chamber: Dark, 5° C.
Detection: 254 nm, and 360 nm
Injection Volume: 25 uL
Mobile Phase A:
 8.95 g Sodium acetate.$3H_2O$
 5.88 mL 1.0 M Tetrabutylammonium hydroxide (TBAH)
 4 L MQ $H_2O$
 pH to 4.6 with glacial acetic acid
 Add 210 mL of Mobile Phase B (below)
Mobile Phase B:
 4 L MeOH
 5.88 mL TBAH
 0.89 mL Glacial acetic acid

| Gradient: | Time(minutes) | Flow mL/min | A % | B % |
| --- | --- | --- | --- | --- |
| | 0 | 1.0 | 100 | 0 |
| | 3 | 1.0 | 75 | 25 |
| | 9 | 1.0 | 60 | 40 |
| | 11 | 1.0 | 0 | 100 |
| | 13 | 1.0 | 0 | 100 |
| | 15 | 1.0 | 100 | 0 |
| | 15.5 | 0.1 | 100 | 0 |

Isolation and Cloning of Genes Encoding Glycerol Dehydratase (dhaB) and 1.3-propanediol oxidoreductase (dhaT)

Methods for the identification and isolation of dhaB and dhaT were done essentially as described in U.S. Pat. No. 5,686,276, hereby incorporated by reference. Cosmid vectors and cosmid transformation methods were used within the context of the present invention to clone large segments of genomic DNA from bacterial genera known to possess genes capable of processing glycerol to 1,3-propanediol. Specifically, genomic DNA from *K. pneumoniae* ATCC 25955 was isolated by methods well known in the art and digested with the restriction enzyme Sau3A for insertion into a cosmid vector Supercos 1 and packaged using GigapackII packaging extracts. Following construction of the vector *E. coli* XL1-Blue MR cells were transformed with the cosmid DNA. Transformants were screened for the ability to convert glycerol to 1,3-propanediol by growing the cells in die presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene (dhaB) from *C. freundii*, demonstrating that these transformants contained DNA encoding the glycerol dehydratase gene.

A 12.1 kb EcoRI-SalI fragment from pKP1, subcloned into pIBI31 (IBI Biosystem, New Haven, CN), was sequenced and termed pHK28-26 (SEQ ID NO:10). Sequencing revealed the loci of the relevant open reading frames of the dha operon encoding glycerol dehydratase and genes necessary for regulation. Referring to SEQ ID NO:10, a fragment of the open reading frame for dhaK (encoding dihydroxyacetone kinase) is found at bases 1–399; the open reading frame dhaD (encoding glycerol dehydrogenase) is found at bases 983–2107; the open reading frame dhaR (encoding the repressor) is found at bases 2209–4134; the open reading frame dhaT (encoding 1,3-propanediol oxidoreductase) is found at bases 5017–6180; the open reading frame dhaB1 (encoding the α subunit glycerol dehydratase) is found at bases 7044–8711; the open reading frame dhaB2 (encoding the β subunit glycerol dehydratase) is found at bases 8724–9308; the open reading frame dhaB3 (encoding the γ subunit glycerol dehydratase) is found at bases 9311–9736; and the open reading frame dhaBX (encoding a protein of unknown function) is found at bases 9749–11572. Additionally, the open reading frame orfY (encoding a protein of unknown function) is found at bases 6202–6630; the open reading frame orfX (encoding a protein of unknown function) is found at bases 4643–4996, and the open reading frame orfW (encoding a protein of unknown function) is found at bases 4112–4642.

Construction of General Purpose Expression Plasmids for Use in Transformation of *Escherichia coli*

Construction of Expression Vector pTacIQ

The *E. coli* expression vector pTacIQ was prepared by inserting lacIq gene (Farabaugh, (1978), *Nature* 274 (5673)

765–769) and tac promoter (Amann et al., (1983), Gene 25, 167–178) into the restriction endonuclease site EcoRI of pBR322 (Sutcliffe, (1979), *Cold Spring Harb. Symp. Quant. Biol.* 43, 77–90). A multiple cloning site and terminator sequence (SEQ ID NO:11) replaces the pBR322 sequence from EcoRI to SphI.

Subcloning the Glycerol Dehydratase Genes (dhaB1, 2, 3, X

The open reading frame for the dhaB3 gene was amplified from pHK 28–26 by PCR using primers (SEQ ID NO:12 and SEQ ID NO:13) incorporating an EcoRI site at the 5' end and a XbaI site at the 3' end. The product was subcloned into pLitmnus29 (New England Biolab, Inc., Beverly, Mass.) to generate the plasmid pDHAB3 containing dhaB3.

The region containing the entire coding region for dhaB1, dhaB2, dhaB3 and dhaBX of the dhaB operon from pHK28–26 was cloned into pBluescriptIIKS+ (Stratagene, La Jolla, Calif.) using the restriction enzymes KpnI and EcoRI to create the plasmid pM7.

The dhaBX gene was removed by digesting plasmid pM7 with ApaI and XbaI, purifying the 5.9 kb fragment and ligating it with the 325-bp ApaI-XbaI fragment from plasmid pDHAB3 to create pM11 containing dhaB1, dhaB2 and dhaB3.

The open reading frame for the dhaB1 gene was amplified from pHK28–26 by PCR using primers (SEQ ID NO:14 and SEQ ID NO:15) incorporating a HindIII site and a consensus ribosome binding site at the 5' end and a XbaI site at the 3' end. The product was subcloned into pLitmus28 (New England Biolab, Inc.) to generate the plasmid pDT1 containing dhaB1.

A NotI-XbaI fragment from pM11 containing part of the dhaB1 gene, the dhaB2 gene and the dhaB3 gene was inserted into pDT1 to create the dhaB expression plasmid, pDT2. The HindIII-XbaI fragment containing the dhaB(1, 2,3) genes from pDT2 was inserted into pTacIQ to create pDT3.

Subcloning the 1.3-propanediol Dehydrogenase Gene (dhaT)

The KpnI-SacI fragment of pHK28–26, containing the 1,3-propanediol dehydrogenase (dhaT) gene, was subcloned into pBluescriptII KS+ creating plasmid pAH1. The dhaT gene was amplified by PCR from pAH1 as template DNA and synthetic primers (SEQ ID NO:16 with SEQ ID NO:17) incorporating an XbaI site at the 5' end and a BamHI site at the 3' end. The product was subcloned into pCR-Script (Stratagene) at the SrfI site to generate the plasmids pAH4 and pAH5 containing dhaT. The plasmid pAH4 contains the dhaT gene in the right orientation for expression from the lac promoter in pCR-Script and pAH5 contains dhaT gene in the opposite orientation. The XbaI-BamHI fragment from pAH4 containing the dhaT gene was inserted into pTacIQ to generate plasmid pAH8. The HindII-BamHI fragment from pAH8 containing the RBS and dhaT gene was inserted into pBluescriptIIKS+ to create pAH11.

Construction of an Expression Cassette for dhaT and dhaB (1, 2, 3)

An expression cassette for dhaT and dhaB(1, 2, 3) was assembled from the individual dhaB(1, 2, 3) and dhaT subclones described previously using standard molecular biology methods. A SpeI-SacI fragment containing the dhaB (1, 2, 3) genes from pDT3 was inserted into pAH11 at the SpeI-SacI sites to create pAH24. A SalI-XbaI linker (SEQ ID NO:22 and SEQ ID NO:23) was inserted into pAH5 which was digested with the restriction enzymes SalI-XbaI to create pDT16. The linker destroys the XbaI site. The 1 kb SalI-MluI fragment from pDT16 was then inserted into pAH24 replacing the existing SalI-MluI fragment to create pDT18. pDT21 was constructed by inserting the SalI-NotI fragment from pDT18 and the NotI-XbaI fragment from pM7 into pCL1920 (SEQ ID NO:24). The glucose isomerase promoter sequence from Streptomyces (SEQ ID NO:25) was cloned by PCR and inserted into EcoRI-HinDIII sites of pLitmus28 to construct pDT5. pCL1925 was constructed by inserting EcoRI-PvuII fragment of pDT5 into the EcoRI-PvuI site of pCL1920. pDT24 was constructed by cloning the HinDIII-MluII fragment of pDT21 and the MluI-XbaI fragment of pDT21 into the HinDIII-XbaI sites of pCL1925.

Example 1

Construction Of Expression Cassette for $B_{12}$ Transport Genes

Expression plasmids that could exist as replicating elements were constructed for the four $B_{12}$ transport genes, btuB, btuC, btuD, and btuE. All expression plasmids use a trc promoter for transcription Each plasmid also contained either a gene for β-lactamase for selection in *E. coli* on media containing ampicillin, or a gene encoding chloramphenicol acetytransferase for selection on media containing chloramphenicol. Plasmid origins of replication are either ColE1 or p15A.

The btuB gene was amplified from *E. coli* chromosomal DNA by PCR using primers (SEQ ID NO:18 with SEQ ID NO:19) which adds an NcoI site at the 5' end and a BamHI site at the 3' end. Reaction mixture contained 10 mM Tris pH 8.3, 50 mM KCl, 1.5 mM $MgCl_2$, 0.0001% gelatin, 200 $\mu$M dATP, 200 $\mu$M dCTP, 200 $\mu$M dGTP, 200 $\mu$M dTTP, 1$\mu$M each primer, 1–10 ng target DNA, 25 units/mL Amplitaq™ DNA polymerase (Perkin-Elmer Cetus, Norwalk Conn.). PCR parameters were 1 min at 94° C., 1 min at 52° C., 2 min at 72° C., 25 cycles. The 1905 bp PCR product was cloned between the NcoI and BamHI sites of plasmid pTrc99A (Pharmacia, Piscataway, N.J.) to generate the plasmid pBtuB 1. Plasmid pBtuB I has a ColE1 origin of replication, ampicillin resistance a lacIq gene, and btuB is expressed from Ptrc.

To construct plasmid pBtuB2, an SphI/BamHI fragment encoding lacIq, Ptrc, and btuB was removed from pBtuB1 and cloned into the SphI/BamHI sites of plasmid pACYC184. Plasmid pBtuB2 has a p15A origin of replication, chloramphenicol resistance a lacIq gene, and btuB is expressed from Ptrc.

The btuCED genes were amplified from *E. coli* chromosomal DNA by PCR using primers (SEQ ID NO:20 with SEQ ID NO:21) which adds a BamHI site at the 5' end and a HindIII site at the 3' end. The 2557 bp PCR product was cloned between the BamHI and HindHIII sites of pACYC184 to generate the plasmid pCED. Plasmid pCED has a P15A origin of replication and a chloramphenicol resistance gene.

To construct plasmid pBCED an Sph/BamHI fragment encoding lacIq, Ptrc and btuB was removed from pBtuB1 and cloned into the SphI/BamHI sites of pCED. Plasmid pBCED has a p15A origin of replication, chloramphenicol resistance, a lacIq gene, and the btu genes in the order btuBCED downstream from a trc promoter.

Example 2

Transformants Containing Genes for $B_{12}$ Transport and DhaB Activity

E. coli strain FM5 was transformed with the dha plasmid pDT24 (specR), the btuB plasmids pBtuB1 (ampR) or pBtuB2 (chlR), or the btuBCED plasmid pBCED (chlR). Selection is on LB plates containing 50 mg/L spectinomycin, 50 mg/L ampicillin or 100 mg/L chloramphenicol. Colonies resistant to the appropriate antibiotics were used for 1,3-propanediol production and vitamin or coenzyme $B_{12}$ uptake.

Example 3

Increased Uptake of Coenzyme $B_{12}$ in FM5 Transformed with pBCED

The appropriate strains were grown overnight at 37° C., shaking at 250 rpm, in 250 mL baffled flasks containing 25 mL of broth (broth, titrated to pH 6.8 with $NH_4OH$, contained 0.2 M $KH_2PO_4$, 2.0 g/L citric acid, 2.0 g/L $MgSO_4.7H_2O$, 1.2 mL 98% $H_2SO_4$, 0.30 g/L ferric ammonium citrate, 0.20 g/L $CaCl_2.2H_2O$, 5 mL of trace metal mix, 5 g/L yeast extract, 10 g/L D-glucose, and appropriate antibiotics. Trace metal mix contained (g/L): $Na_2SO_4$ (4.0), $MnSO_4.H_2O$ (0.80), $ZnSO_4.7H_2O$ (1.6), $CoSO_4$ (0.52), $CuSO_4.5H_2O$ (0.12), and $FeSO_4.7H_2O$ (4.0)). Dilutions (1/100) of the overnight cultures were made into 25 mL M9 broth flasks and growth continued until an $OD_{660} \sim 1.0$ was reached. When IPTG was added, it was added at this point to 0.2 mM, and incubation was continued for 1 hr.

Cyanocobalamin (cyanocobalamin, CNCbl) or coenzyme $B_{12}$ was added to the M9 cultures at the concentrations. All procedures involving coenzyme $B_{12}$ were performed in the dark (red light). One mL samples were withdrawn immediately upon addition of cobalamin and the cells were pelleted. The cultures were then allowed to incubate further with 250 rpm shaking until endpoint samples were taken as given in Table 1 and Table 2, below.

Cell-free supernatants from each one mL sample were run on HPLC for cobalamin quantification. Cobalamin quantification was achieved by first comparing peak area ratios at 278 nm and 361 nm with standards, and then applying peak areas to standard curves of the cobalamins.

Endpoint analysis involved cell separation from media, followed by separation of periplasm from cytoplasm. Methods followed essentially those of Kaback (*Methods of Enzymology* vol. 22, pg. 99, 1971).

Recovered cell pellets were weighed, and washed 2X with 10 mM Tris, pH 8.0. Pellets were resuspended at 1 g/80 mL of 30 mM Tris, pH 8.0/20% sucrose. While stirring on a magnetic stir plate, EDTA was added to 10 mM and lysozyme to 0.5 mg/mL. These suspensions were stirred at room temperature for 30 minutes. Following this lysozyme/EDTA incubation, cells clumped, and sedimented as expected. Each suspension was pelleted at 15K rpm for 20 minutes at 4° C. Supernatants, now consisting of diluted periplasm, were collected, volumes noted, and samples taken for HPLC analysis.

Recovered spheroplast pellets were homogenized into 3 mLs 50 mM potassium phosphate buffer, pH 7.0 using a tissue homogenizer. Once homogenized, Dnase and Rnase were added to 5 mg/mL, and suspensions incubated in a 37° C. water bath. EDTA was added to 10 mM, and the incubation continued for 15 minutes. $MgSO_4$ was added to 15 nM, and the incubation continued for 15 minutes.

Resulting suspensions were ultracentrifuged at 39K rpm for 1 hour at 4° C. Supernatants, now consisting of diluted cytoplasm, were collected, volumes noted, and sampled for HPLC analysis.

Periplasm and cytoplasm concentrations of cobalamin were calculated using the assumptions that: 1 ug of cells (wet weight) is equivalent to 1,000,000 cells, the volume of a cell is $9 \times 10^{-13}$ mL, and the periplasmic volume equals 30% of the total cell volume.

TABLE 1

Effect of pBtuB1A on uptake of 5 uM cyanocobalamin in strain FM5

| Strain | Time (hr) | Periplasm | Cytoplasm |
|---|---|---|---|
| FM5 | 16 | 6 uM | 6.5 uM |
| FM5/pBtuB1 | 16 | 196 uM | 45.0 uM |

TABLE 2

Effect of pBCED on uptake of 10 uM coenzyme $B_{12}$ in strain FM5

| Strain | Time (hr) | Broth | Periplasm | Cytoplasm |
|---|---|---|---|---|
| FM5/pBtuB2 + IPTG | 0 | 9.7 uM | | |
| | 16 | Below Detection Limit | 840 uM | 82 uM |
| FM5/pBCED + IPTG | 0 | 10 uM | | |
| | 16 | Below Detection Limit | 280 uM | 170 uM |

Example 4

Increased production of 1.3-propanediol from FM5/pDT24 transformed with pBCED

E. coli strains FM5/pDT24 and FM5/pDT24/pBCED were cultured in 250 mL flasks containing 25 mL of medium at 30° C., protected from light and shaking at 250 rpm. Medium, titrated to pH 6.8 with $NH_4OH$, contained 0.2 M $KH_2PO_4$, 2.0 g/L citric acid, 2.0 g/L $MgSO_4.7H_2O$, 1.2 mL 98% $H_2SO_4$, 0.30 g/L ferric ammonium citrate, 0.20 g/L $CaCl_2.2H_2O$, 5 mL of trace metal mix, 5 g/L yeast extract, 10 g/L D-glucose, and 30 g/L glycerol. Trace metal mix contained (g/L): $Na_2SO_4$ (4.0), $MnSO_4.H_2O$ (0.80), $ZnSO_4.7H_2O$ (1.6), $CoSO_4$ (0.52), $CuSO_4.5H_2O$ (0.12), and $FeSO_4.7H_2O$ (4.0). In addition, pDT24 and pBCED required 50 ug/mL spectinomycin and 20 ug/mL chloramphenicol, respectively.

FM5/pDT24 and FM5/pDT24/pBCED were grown as described above with the addition of cyanocobalamin, hydroxocobalamin (hydroxy $B_{12}$), or coenzyme $B_{12}$ to a final concentration of either 0.40 uM or 4.0 uM. Flasks were inoculated to an initial OD600 of approximately 0.01 AU, pH was maintained above pH 6.2 with the addition of 0.5 N KOH, and the glucose concentration was maintained above 2 g/L with the addition of a 50% (w/w) solution. pH was monitored using ColorpHast strips (EM Science, Gibbstown, N.J.). Glucose concentration was monitored using the Trinder enzymatic assay (Sigma, St. Louis, Mo. At various times, aliquots were removed in order to determine 3G concentration (hplc analysis) and cell density ($OD_{600}$). The results are shown in Tables 3 and 4 below.

TABLE 3

Effect of pBCED on the production of 1,3-propanediol in the presence of 0.40 uM cyanocobalamin, hydroxocobalamin, and coenzyme $B_{12}$

| | | FM5/pDT24 | | FM5/pDT24/pBCED | |
|---|---|---|---|---|---|
| $B_{12}$ Addition (0.4 uM) | TIme (hr) | 1,3-Propanediol (g/L) | OD600 (AU) | 1,3-Propanediol (g/L) | OD600 (AU) |
| Cyanocobalamin | 0 | 0.0 | 0.1 | 0.0 | 0.0 |
| " | 9 | 0.0 | 6.3 | 0.3 | 6.9 |
| " | 11 | 0.0 | 9.4 | 1.0 | 10.0 |
| " | 12 | 0.0 | 9.7 | 1.0 | 9.9 |
| " | 14 | 0.0 | 11.6 | 1.2 | 12.5 |
| " | 17 | 0.0 | 19.4 | 1.2 | 19.3 |
| " | 19 | 0.0 | 24.8 | 1.2 | 24.1 |
| " | 33 | 0.0 | 41.5 | 0.9 | 46.5 |
| Hydroxy $B_{12}$ | 0 | 0.0 | 0.1 | 0.0 | 0.0 |
| " | 9 | 0.1 | 6.2 | 1.0 | 6.1 |
| " | 11 | 0.3 | 8.8 | 2.0 | 8.3 |
| " | 12 | 0.3 | 9.7 | 2.2 | 9.1 |
| " | 14 | 0.3 | 10.4 | 2.3 | 10.5 |
| " | 17 | 0.4 | 17.3 | 2.3 | 15.8 |
| " | 19 | 0.4 | 22.0 | 2.2 | 18.2 |
| " | 33 | 0.2 | 41.5 | 1.5 | 35.8 |

TABLE 4

Effect of pBCED on the production of 1,3-propanediol in the presence of 4.0 uM cyanocobalamin, hydroxocobalamin, and coenzyme $B_{12}$

| | | FM5/pDT24 | | FM5/pDT24/pBCED | |
|---|---|---|---|---|---|
| $B_{12}$ Addition (4.0 uM) | TIme (hr) | 1,3-Propanediol (g/L) | OD600 (AU) | 1,3-Propanediol (g/L) | OD600 (AU) |
| Cyanocobalamin | 0 | 0.0 | 0.2 | 0.0 | 0.1 |
| " | 8 | 0.1 | 8.9 | 0.4 | 9.7 |
| " | 10 | 0.1 | 11.9 | 0.8 | 11.6 |
| " | 12 | 0.3 | 13.7 | 1.5 | 15.9 |
| " | 14 | 0.8 | 17.8 | 3.3 | 23.0 |
| " | 16 | 1.3 | 24.7 | 6.1 | 29.6 |
| " | 33 | 1.6 | 36.6 | 10.2 | 40.7 |
| Hydroxy $B_{12}$ | 0 | 0.0 | 0.1 | 0.0 | 0.1 |
| " | 8 | 0.4 | 9.0 | 1.7 | 9.5 |
| " | 10 | 1.3 | 11.5 | 2.7 | 12.2 |
| " | 12 | 2.8 | 12.9 | 3.8 | 14.6 |
| " | 14 | 4.2 | 16.1 | 5.4 | 18.9 |
| " | 16 | 5.5 | 19.9 | 7.2 | 25.1 |
| " | 33 | 7.3 | 49.1 | 13.1 | 43.8 |

We claim:

1. A process for the bio-production of 1,3-propanediol comprising:

(i) contacting a transformed host cell with at least one fermentable carbon source and an effective amount of at least one compound selected from the group consisting of cyanocobalamin, hydroxocobalamin, and aquacobalamin whereby 1,3-propanediol is produced, the transformed host cell comprising:

(a) at least one copy of a gene encoding a protein having a dehydratase activity;
(b) at least one copy of a gene encoding a protein having an oxidoreductase activity;
(c) at least one copy of a gene encoding a vitamin B12 receptor precursor protein;
(d) at least one copy of a gene encoding a vitamin B12 transport system permease protein; and
(e) at least one copy of a gene encoding vitamin B12 transport ATP- or GTP-binding protein;

wherein the vitamin B12 receptor precursor protein encoded by the gene of element (c) is disrupted whereby its coenzyme B12 binding sites are not regulated by the intracellular concentration of coenzyme B12; and (ii) recovering the 1,3-propanediol produced from step (i).

2. The process of claim 1 wherein the gene encoding a protein having a dehydratase activity of step 1(a) encodes an enzyme selected from the group consisting of a glycerol dehydratase enzyme and a diol dehydratase enzyme.

3. The process of claim 1 wherein the individual genes of 1(a) and 1(b) are independently isolated from the group of microorganisms consisting of Klebsiella sp., Citrobacter sp., Salmonella sp., and Clostridium sp.

4. The process of claim 1 wherein the individual genes of 1(c), 1(d), and 1(e) are independently isolated from the group of microorganisms consisting of Escherichia sp., Salmonella sp., Klebsiella sp., Pseudomonas sp., and Citrobacter sp.

5. The process of claim 1 wherein:
(i) the gene of (i)(c) is a btuB gene selected from the group consisting of SEQ ID NO:1 and SEQ ID NO:2;
(ii) the gene of (i)(d) is a btuC gene of SEQ ID NO:3; and
(iii) the gene of (i)(e) is a btuD gene of SEQ ID NO:4.

6. The process of claim 1 wherein the fermentable carbon source is selected from the group consisting of fermentable carbohydrates, single-carbon substrates, and mixtures thereof.

7. The process of claim 1 wherein the fermentable carbon source is selected from the group consisting of monosaccharides, oligosaccharides, polysaccharides, single carbon substrates, glycerol, dihydroxyacetone and carbon-containing amines.

8. The process of claim 1 wherein the transformed host cell further comprises at least one copy of a gene encoding a glycerol-3-phosphate dehydrogenase enzyme and at least one copy of a gene encoding a glycerol-3-phosphatase enzyme.

9. The process of claim 1 wherein the host cell is selected from the group consisting of bacteria, yeast, and filamentous fungi.

10. The process of claim 9 wherein the host cell is selected from the group of genera consisting of Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces, and Pseudomonas.

11. The process of claim 1 wherein the effective amount of at least one compound selected from the group consisting of cyanocobalamin, hydroxocobalamin, and aquacobalamin is at a 0.1- to 10.0-fold molar ratio to the amount of dehydratase present.

12. A transformed host cell comprising:
(a) at least one copy of a gene encoding a protein having a dehydratase activity;
(b) at least one copy of a gene encoding a protein having an oxidoreductase activity;
(c) at least one copy of a gene encoding a vitamin B12 receptor precursor protein;
(d) at least one copy of a gene encoding a vitamin B12 transport system permease protein; and
(e) at least one copy of a gene encoding vitamin B12 transport ATP- or GTP-binding protein,
wherein the vitamin B12 receptor precursor protein encoded by the gene of element (c) is disrupted whereby its coenzyme B12 binding sites are not regulated by the intracellular concentration of coenzyme B12, and wherein the at least one copy of any of the genes of (c), (d), and/or (e) is introduced into the host cell.

13. A process for the bio-production of 1,3-propanediol comprising:
(i) contacting a transformed host cell with (a) at least one fermentable carbon source selected from the group consisting of monosaccharides, oligosaccharides, polysaccharides, single carbon substrates, glycerol, dihydroxyacetone and carbon-containing amines and (b) an effective amount of at least one compound selected from the group consisting of cyanocobalamin, hydroxocobalamin, and aquacobalamin, whereby 1,3-propanediol is produced, the transformed host cell comprising:
(a) at least one copy of a gene encoding a protein having a dehydratase activity;
(b) at least one copy of a gene encoding a protein having an oxidoreductase activity;
(c) at least one copy of a gene encoding a vitamin $B_{12}$ receptor precursor protein;
(d) at least one copy of a gene encoding a vitamin $B_{12}$ transport system permease protein; and
(e) at least one copy of a gene encoding vitamin $B_{12}$ transport ATP- or GTP-binding protein;
(f) at least one copy of a gene encoding a protein having a glycerol-3-phosphate dehydrogenase activity; and
(g) at least one copy of a gene encoding a protein having a glycerol-3-phosphatase activity,
wherein the at least one copy of the gene of element (i)(c) is introduced into the host cell, and the vitamin B12 receptor precursor protein encoded by the gene of element (i)(c) is disrupted whereby its coenzyme B12 binding sites are not regulated by the intracellular concentration of coenzyme B12; and (ii) recovering the 1,3-propanediol produced from step (i).

* * * * *